(12) United States Patent
Sciortino et al.

(10) Patent No.: US 11,344,183 B2
(45) Date of Patent: May 31, 2022

(54) ATTACHABLE ERGONOMIC BIDIRECTIONAL SELF-LOCKING KNOB-CONTROL ASSISTING APPARATUS FOR AN ENDOSCOPE

(71) Applicant: SergoMED LLC, Ashburn, VA (US)

(72) Inventors: Vincent Sciortino, Merrick, NY (US); Kevin Chang, Charlottesville, VA (US); Vikram Seshadri, Ashburn, VA (US)

(73) Assignee: SergoMED LLC, Ashburn, VA (US)

( * ) Notice: Subject to any disclaimer, the term of this patent is extended or adjusted under 35 U.S.C. 154(b) by 0 days.

(21) Appl. No.: 17/455,092

(22) Filed: Nov. 16, 2021

(65) Prior Publication Data

US 2022/0071480 A1    Mar. 10, 2022

Related U.S. Application Data

(63) Continuation of application No. 17/304,377, filed on Jun. 20, 2021.

(60) Provisional application No. 63/042,053, filed on Jun. 22, 2020.

(51) Int. Cl.
*A61B 1/00* (2006.01)
(52) U.S. Cl.
CPC ................ *A61B 1/00131* (2013.01)
(58) Field of Classification Search
None
See application file for complete search history.

(56) References Cited

U.S. PATENT DOCUMENTS

| 5,330,502 A | 7/1994 | Hassler et al. |
| 2008/0119696 A1* | 5/2008 | Moriyama ........... A61B 1/0052 600/146 |
| 2015/0351610 A1 | 12/2015 | Fan |
| 2016/0089124 A1 | 3/2016 | Morimoto et al. |
| 2017/0281219 A1 | 10/2017 | Hibner et al. |
| 2022/0095892 A1* | 3/2022 | Montenegro ...... A61B 1/00131 |

FOREIGN PATENT DOCUMENTS

| CN | 109157180 A | 3/2021 |
| JP | 4445779 B2 | 4/2010 |
| JP | 4533907 B2 | 9/2010 |
| JP | 3181928 U | 2/2013 |

OTHER PUBLICATIONS

Machine Translation of JP2007096891—Priority Document for JP4533907B2.
(Continued)

*Primary Examiner* — Timothy J Neal
(74) *Attorney, Agent, or Firm* — Vance Intellectual Property, PC

(57) ABSTRACT

The present invention relates to an ergonomic bidirectional self-locking mechanism for endoscope angulation control knob operation, which allows for easier access to the endoscope control knobs, reduced muscle exertion for knob operation, and real-time locking of the position of the knobs when turned, as disclosed herein. The invention has benefits for the operator thereof from ergonomic and patient safety perspectives.

21 Claims, 20 Drawing Sheets

(56) References Cited

OTHER PUBLICATIONS

Machine Translation of JP2004056869—Priority Document for JP4445779B2.
English Translation of JP3181928U: https://patents.google.com/patent/JP3181928U/en?q=endoscope+knob+attachment&oq=endoscope+knob+attachment&page=2.
English Translation of CN109157180A https://patents.google.com/patent/CN109157180A/en?q=endoscope+ratchet&oq=endoscope+ratchet.
PCT/US2021/70732 International Search Reports dated Nov. 8, 2021 (corresponding PCT application).
PCT/US2021/70732 Written Opinion of the International Searching Authority dated Nov. 8, 2021 (corresponding PCT application).

\* cited by examiner

ATTACHABLE ERGONOMIC BIDIRECTIONAL SELF-LOCKING KNOB-CONTROL ASSISTING APPARATUS FOR AN ENDOSCOPE

FIELD OF THE INVENTION

The current invention relates to medical devices, and more particularly, to endoscopes. In one aspect, it concerns a bidirectional self-locking mechanism for endoscope angulation control knob operation. The invention provides a novel mechanical system for easier access to the endoscope control knobs, reduced muscle exertion for knob operation, and real-time locking of the position of the knobs when turned, as disclosed herein. The invention has benefits for the operator thereof from ergonomic and patient safety perspectives.

BACKGROUND OF THE INVENTION

The flexible endoscope is an essential tool used in the field of gastroenterology to diagnose and treat patients. One form of endoscopy, the colonoscopy, is performed at a minimum of 19 million times annually in the US alone to identify colorectal polyps and cancers. Due to a high demand for endoscopic procedures, gastroenterologists are at a high risk of developing musculoskeletal overuse injuries due to the mechanical challenges posed by operating the modern endoscope. One of the more common endoscopy-specific overuse injuries is De Quervain's tenosynovitis, which leads to acute pain in the left thumb due to an inflammation in the abductor pollicis longus (APL) and extensor pollicis brevis (EPB).

Currently, the flexible endoscope is operated by holding the endoscope handle with the operator's left hand and turning the angulation control knobs of the endoscope that, when turned, flexes the distal end of the scope. In the current mode of operation, the left hand of the operator is used to hold the endoscope while the left thumb and fingers turn the angulation knobs, while the right hand is responsible for advancing and withdrawing the distal endoscope tubing in/out the patient's body. The current design of the endoscope is ergonomically flawed because the force required to turn the endoscope knobs exceeds the safety threshold, with the peak thumb force recorded with a force sensor at 13.8 Newtons in colonoscopy procedures, which lead to repetitive strain injury (Shergill 2016, "886 Ergonomic Evaluation of Colonoscopy: Assessment of Biomechanical Risk Factors Associated With Distal Upper Extremity Musculoskeletal Disorders in Endoscopists Performing Routine Colonoscopy"). The left forearm muscle activation recorded with an electromyograph also exceeds the safety threshold at 30.1% of maximum voluntary contraction (Shergill 2016, supra). When turning the endoscope angulation control knobs, the left hand is often required to sustain exertion on the knobs in order to maintain scope flexion against the natural recoil of the knobs to its neutral position. Although endoscope knobs have switch locks that can be engaged to lock knobs in place, they not only require the operator to engage the switch with a second hand, but the switch locks are only viable for maintaining the flexed position at the time of engaging the switch. In this state, it is possible yet very difficult to continue turning the knob after it has been locked in place due to the increased resistance after a switch lock is engaged. The current flexible endoscope cannot continuously self-lock each position of the knob as it is being turned in real-time, which raises the necessity for the left hand to frequently sustain exertion. Over time, the large forces required to turn the knobs and the frequent necessity to hold strenuous knob positions can lead to musculoskeletal overuse injuries of the left thumb.

CN109157180A discloses an internal ratcheting system that replaced the current angulation knob control system on the modern endoscope by using a lever-like ratchet regulation piece for each of the two internal angulation mechanisms. Although the system achieves a one-hand real-time locking mechanism, it alters the present operating techniques of the endoscope due to the elimination of the angulation knobs, and it would require a remodeling of the internal endoscope angulation control structure of modern endoscopes. Wang et al. (U.S. Pat. No. 10,617,283 B2) introduced another self-locking mechanism that can achieve real-time stepless angulation locking, but this invention cannot achieve flexion in the up/down and left/right directions, and it also requires a complete redesign of the endoscope. JP4533907B2 discloses a left/right knob attachment that increases the radius of the left/right knob so that doctors with small hands can reach the left/right knob. However, the attachment does not sufficiently address the root ergonomic problem as endoscopists still need to exert and sustain large forces during endoscope operations with the left thumb. Furthermore, the attachment does not offer a solution for the up/down endoscope knob at all. Similarly, JP3181928U, EP1757217B1, and JP4445779B2 each described a left/right knob cover that improves operational feeling, but it also does not sufficiently address ergonomics, especially for the up/down control knob. WO2020183366A1 disclosed a redesigned pair of endoscope knobs with different dimensions and grooves for better grip, but the knobs would require a redesign of the endoscope control handle and still offers no customizability to the individual physician user to improve ergonomics. CN104757930B presented a motor-driven system that completely encapsulates the endoscope handle and the angulation control knobs. Collins et al. (GB2555111A), Gumbs et al. (U.S. Pat. No. 9,706,907 B2) and Olds et al. (WO2012037257A3) each presented a similar motor-driven system that allows the remote robotic operation of the endoscope. However, these motor-driven mechanisms can pose safety risks to patients, and they would additionally require physicians to forgo a vast amount of intensive training to learn a new system. Evidently, a system that addresses the root ergonomic problem and can be easily implemented, while requiring minimum changes to the current system, is desired.

SUMMARY OF THE INVENTION

The present invention adopts the following technical solutions to address the drawbacks of prior art endoscopes.

In one aspect, the present invention provides a mechanical solution to the ergonomic drawbacks of the endoscopes known in the art. For example, it comprises an angulation control knob-mating feature (e.g., knob masks) that interfaces with a bidirectional self-locking mechanism that can be toggled to allow rotation in either the clockwise and counterclockwise direction. In one aspect, the knob masks of the present invention are designed to improve the operator's left hand access to the angulation control knobs of the endoscope handle to reduce the risk of musculoskeletal overuse injuries. In another example, the locking feature of the present invention is also designed to relieve musculoskeletal strain on the operator's left hand by holding the position of the knob at a set number of gradated locations when it is turned, thereby relieving the equivalent exertion required by the left thumb.

In one aspect, the present knob masks are designed to snap fit onto the up/down and left/right angulation control knobs of an endoscope by pressing the knob masks over the knobs from the top. The mating feature for each knob mask comprises, for example, three interfaces that are designed to wrap around the protrusions of the knobs by sliding over the knobs from the top. Each interface contains a cavity that is wider on the bottom side and gradually shortens and closes off at the top. This sloped cavity design allows the knob mask interface to slide over the endoscope angulation control knobs and snap into place.

In one aspect, the knob mask of the present invention also provides teeth-like protrusions around the outer side of its circumference, or in one aspect, situate on top of the knob mask, which interact with the self-locking mechanism.

In one aspect, the self-locking assembly is ratchet-based and comprises three layers and a lid. The bottom layer comprises two cylindrical cavities that are used to house two pawls, respectively, that reach outward toward the ratchet teeth to engage the locking activity. Two reset springs are positioned between the outward side of each of the two pawls and the inner side of the bottom layer side wall. A cylindrical toggle is fitted into a cylindrical hole between the two pawls and interacts with the pawls to allow rotation in one direction and not the other. The top layer utilizes a similar design layout as the bottom layer. The top and bottom layers are divided by a flat middle layer piece that contains a central hole that allows the cylindrical part of the toggle switch to slide through and secure itself in the middle of the two pawls. This middle layer also provides a thin rectangular opening where the switch of the toggle mechanism can protrude and be accessed by the fingers. The lid of the mechanism slides on above the top layer and also contains a central hole in which the cylindrical part of the toggle switch can fit through. Finally, the whole mechanism is then slid into the cavity of the housing unit and capped with a flat capping piece.

In one aspect, the self-locking mechanism is detent-based and comprises a housing unit for the assembly, one or more fasteners to secure the self-locking mechanism to the endoscope, a housing body further comprising a first and second detent piston that each interact with a spring and a first and second respective toggle to push forward the first and second detent pistons, to engage or disengage the communication between the first and second detent pistons with the teeth-like protrusions of the respective first and second masks, allowing control over the bidirectional rotation and locking the angulation control knobs of the endoscope in place.

In one aspect, the housing unit of the present invention provides a cavity into which the locking mechanism can slide and fit snugly. In one aspect, the bottom part of the housing unit also wraps around the endoscope handle and is fastened around the endoscope using, for example, a hook and loop strap. The housing unit is also secured onto the arch attachment piece at its topmost surface through, for example, nuts and bolts, stabilizing the self-locking mechanism against the ratchet teeth. Alternatively, the housing unit can be secured onto the endoscope through two securing hoops that snugly wrap around the endoscope to mate the device with the housing unit: the left/right angulation lock hoop and the valve hoop. The left/right angulation lock hoop is a circular sized hoop that protrudes from an overhang portion of the housing lid of the housing unit and wraps snugly around the circumference of the left/right angulation lock of the endoscope. The valve hoop is an irregularly shaped hoop that wraps around air/water and suction valves, as well as one of the remote switches that rest on the side of the endoscope, firmly securing the housing unit to the endoscope.

In one aspect, the arch attachment piece of the present invention is connected to the housing unit and is supported onto the endoscope by wrapping around the thicker end of the endoscope boot and secured using a hook and loop strap.

The present invention can offer one or more advantages over the prior art. By introducing a strain-reducing apparatus to increase the operator's left-hand access to the endoscope angulation control knobs and incorporate a bidirectional self-locking mechanism, the ergonomics of operating the endoscope are improved, which reduces the risk of developing repetitive strain injuries. The present self-locking mechanism allows engagement and disengagement of the locking mechanism using the same hand that rotates the endoscope angulation knobs, which is an improvement from the current endoscope design which typically requires the operator to use two hands to activate the endoscope's locking feature. In one aspect, the present invention comprises an apparatus kit that is attachable, and it poses a minimum change to the present operating techniques of the endoscope, which offers a seamless integration into the operator's current clinical practice. By introducing the real-time self-locking mechanism, the procedures can be made more precise, which ultimately improves patient safety by reducing the likelihood of physician errors.

In one aspect, the invention concerns an endoscope modified with an attachment apparatus for mechanically assisting the operation of endoscope angulation control knobs, said apparatus comprising:
  (a) one or more knob masks mounted onto or around an at least one endoscope angulation control knob with an at least one tooth-like protrusion around its outer circumference that are in communication with a self-locking mechanism, with one or more knob masks further comprising at least one thumb interface that offer easier access to the knob masks.
  (b) a self-locking mechanism comprising an at least one pawl member that communicates with the at least one tooth-like protrusion of the angulation control knob masks to lock the endoscope angulation control knob position in place; and
  (c) one or more toggles that provide engagement with the at least one pawl member while disengaging with its adjacent pawl member, by communicating with the at least one pawl member with at least one tooth-like protrusion of the angulation control knob mask while freeing its adjacent pawl member from communicating with the teeth-like protrusion of the angulation control knob mask, allowing rotation in one direction while prohibiting rotation in the other; and
  (d) at least one securing means for the apparatus to the endoscope that releasably secures the apparatus to the endoscope.

In one aspect, the invention concerns an endoscope modified with an attachment apparatus for mechanically assisting the operation of endoscope angulation control knobs, said apparatus comprising:
  (a) one or more knob masks mounted onto or around an at least one endoscope angulation control knob with an at least one tooth-like protrusion around its outer circumference that are in communication with a self-locking mechanism, with one or more knob masks further comprising at least one thumb interface that offer easier access to the knob masks.

(b) a self-locking mechanism comprising at least one detent member that communicates with the at least one tooth-like protrusion of the angulation control knob masks to lock the endoscope angulation control knob position in place; and (c) one or more toggles that communicate with at least one detent member that controls the engagement and disengagement of the detent member to the teeth-like protrusion of the angulation control knob masks; and (d) at least one securing means for the apparatus to the endoscope that releasably secures the apparatus to the endoscope.

In one aspect, the invention concerns an attachment apparatus for an endoscope comprising:

(a) a strain reducing means for reducing the forces experienced on the thumb of the operator by about 30-80% measured using a force sensor attached to the operator's thumb or reducing the thumb muscle activation of the operator's thumb by about 50-80% measured using an electromyograph attached to the operator's forearm while the operator is rotating the angulation control knobs of the endoscope;

(b) a self-locking means for resisting the torsion experienced in the endoscope angulation control knobs when the endoscope angulation control knobs are turned away from a neutral position, wherein the torsion within the endoscope angulation control knob's endoscope wires, when not resisted, will return the endoscope angulation control knobs to their neutral position; and (c) A securing means for securing the attachment apparatus to the endoscope.

BRIEF DESCRIPTION OF THE INVENTION

Figure 1:
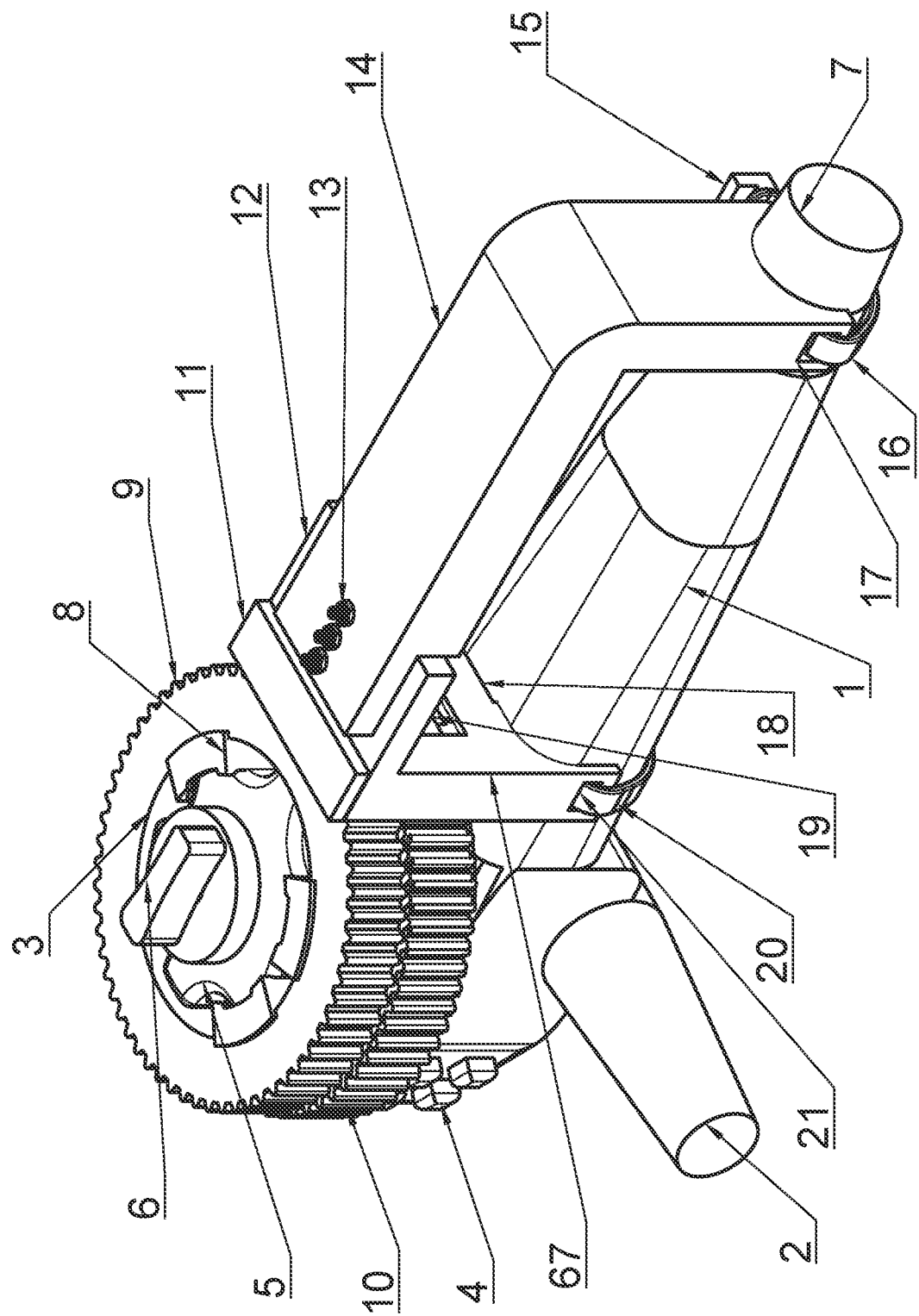
FIG. 1 is a perspective view of one aspect of the present invention installed onto the endoscope handle.

DETAILED DESCRIPTION OF THE INVENTION:

Definitions:

For the purposes of the present invention, an "endoscope" is a medical device that comprises a thin, long flexible tube with a lens system at its distal tip, a working channel within the tubing for insertion of interventional devices, and a control handle with an angulation control system to steer the distal tip used to examine the interior of the human body. Examples of endoscopes contemplated herein include, without limitation: Olympus GIF-H180 Gastroscope, Olympus CF-HQ190L/I Colonoscope, Olympus TJF-Q190V Duodenoscope, PENTAX EC-2990Li Video Colonoscope, Pentax EC-3890Li Video Colonoscope, PENTAX EG27-i10 Video Gastroscope, PENTAX ES-3870K Video Sigmoidoscope, PENTAX ED34-i10T2 Video Duodenoscope, Fujifilm EC-760R-V/L Standard Colonoscope, Fujifilm EG-760R Standard Gastroscope, Fujifilm ES-530WE Video Sigmoidoscope, Fujifilm ED-580XT Duodenoscope, Boston Scientific EXALT Model D Single-Use Duodenoscope, KARL STORZ Flexible SILVER SCOPE Gastroscopes, KARL STORZ Flexible SILVER SCOPE® Colonoscopes, KARL STORZ HyDome™ Duodenoscopy System.

An "attachment apparatus" is a medical device that is attachable to an endoscope.

A "knob mask" is a unit of the attachment apparatus that mates with its corresponding endoscope angulation control knob, which rotates in unison when turned. The knob mask uses anchor ports that slide over at least one of the protrusions of the endoscope angulation control knobs. The knob mask also contains teeth-like protrusions that are used to interact with the pawls of the self-locking mechanism or detent pistons of a detent self-locking mechanism to perform self-locking action.

A "first mask" is a knob mask that mates with the up/down angulation control knob of the endoscope and rotates in unison with the up/down angulation control knob when turned.

A "second mask" is a knob mask that mates with the left/right angulation control knob of the endoscope and rotates in unison with the left/right angulation control knob when turned.

An "anchor port" is a part of the inner circumference of the knob mask and is shaped to match the contour of the endoscope angulation control knob so that the knob mask can mate with the endoscope angulation control knob so that they rotate in unison. The mating occurs by the anchor port sliding over the endoscope angulation control knob, anchoring the knob mask to the endoscope angulation control knob.

A "self-locking mechanism" is a mechanical system of actuators, pawls, detents, toggles, and its respective housing units that interface with the knob mask to lock the endoscope angulation control knob in place when turned to a certain degree. In one aspect, the self-locking mechanism comprises at least one knob mask, at least one pawl member that communicates with the teeth-like protrusions on the outer circumference of the knob mask, at least one toggle that communicates with the pawl member, at least one housing unit for the self-locking mechanism's assembly, and at least one securing means that secures the apparatus to the endoscope. In one aspect, the self-locking mechanism comprises at least one knob mask, at least one detent member that communicates with the teeth-like protrusions on the outer circumference of the teeth ring on top of the knob mask, at least one toggle that communicates with the at least one detent member, and at least one housing unit for the self-locking mechanism's assembly, and at least one fastener that secures the apparatus to the endoscope.

A "first detent piston" is a detent member configured to communicate with the teeth-like protrusions on the first mask to lock the position of the first mask, thereby locking the position of the up/down endoscope angulation control knob.

A "second detent piston" is a detent member configured to communicate with the teeth-like protrusions on the second mask to lock the position of the second mask, thereby locking the position of the left/right endoscope angulation control knob.

A "toggle" is a unit assembled inside the self-locking mechanism to control bidirectional locking. In one aspect, the toggle activates or deactivates the direction in which the self-locking mechanism can lock. In one aspect, the toggle comprises leaflets around its central cylindrical piece which interacts with none or only one of the pawls of the self-locking mechanism assembly. In one aspect, the toggle is used to engage/disengage the detent-based self-locking mechanism, by interacting with a system of detent pistons and springs.

A "strain-reducing means" comprises the means in which the strain imparted on the left thumb of the endoscope operator, and/or the muscle activation involved with using the thumb to turn the endoscope angulation control knobs, is reduced. In one aspect, the strain-reducing means comprises a means in which the forces experienced on the thumb of the operator is reduced by about 30-80% measured using a force sensor attached to the operator's thumb or in which the thumb muscle activation of the operator's thumb is reduced by about 50-80% measured using an electromyograph attached to the operator's forearm while the operator is rotating the angulation control knobs of the endoscope.

A "self-locking means" comprises the means in which the endoscope angulation control knobs lock the position to which they are turned without the need of any action other than the act of turning the knobs. In one aspect, the self-locking means comprises a means in which the torsion experienced in the endoscope angulation control knobs when the endoscope angulation control knobs are turned away from a neutral position is resisted, wherein the torsion within the endoscope angulation control knob's endoscope wires, when not resisted, will return the endoscope angulation control knobs to their neutral position.

A "securing means" comprises a means in which the attachment apparatus is secured to the endoscope.

Modified Endoscopes:

The present invention is shown in detail in FIGS. 1-20 and described below.

The present invention is aimed to reduce the risk of developing left hand repetitive strain injuries or risks to patient safety by modifying the endoscope with an attachable apparatus kit that would aid the operation of the endoscope handle 1, left/right angulation control knob 5, and up/down angulation control knob 22. The present invention is able to mitigate the risk of repetitive strain injuries by reducing the force exerted by the thumb, improving accessibility and leverage of the angulation control knobs, and reducing the duration of thumb muscle usage.

Figure 2:
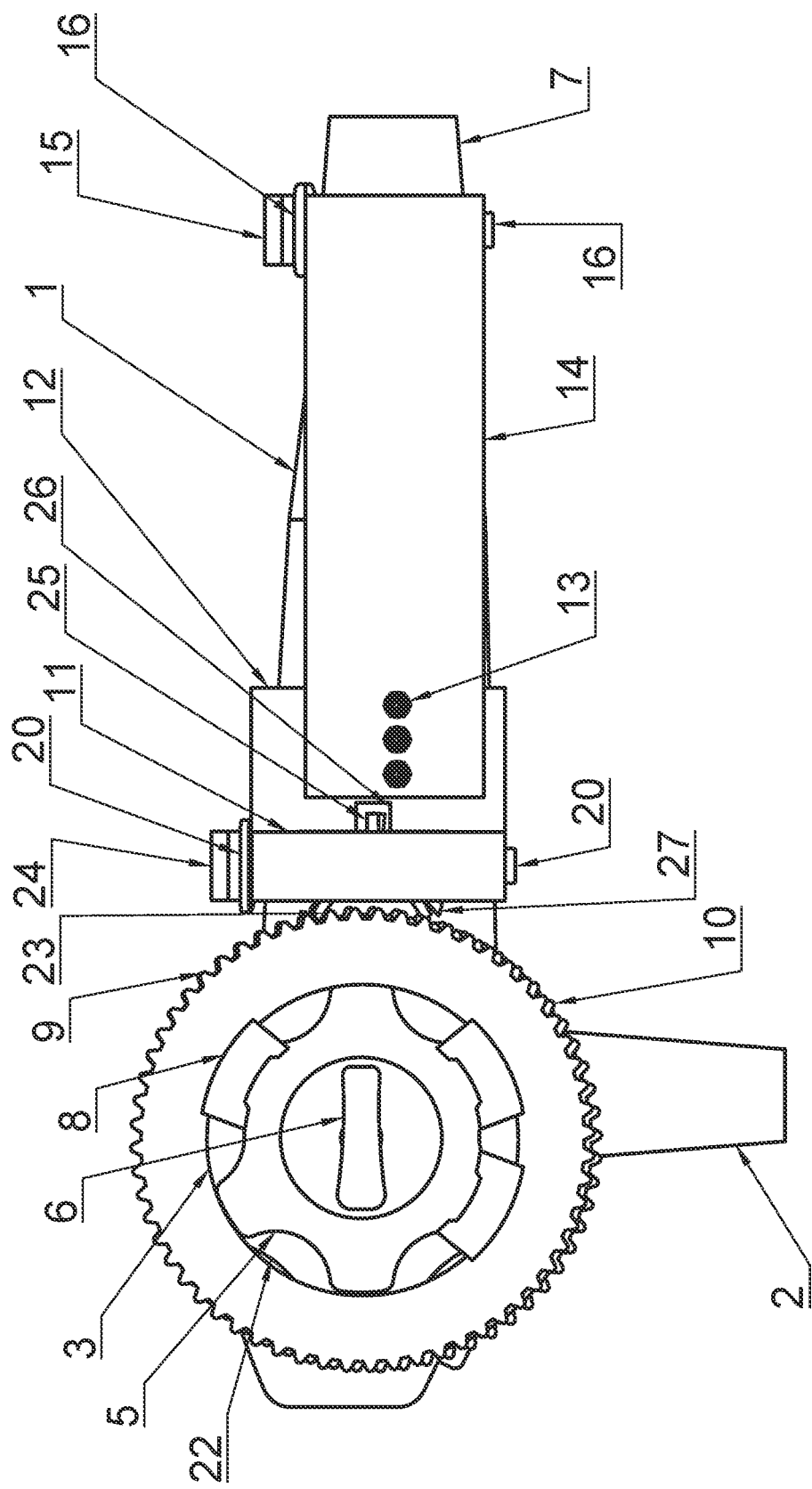
FIG. 2 is a top view of the aspect displayed in FIG. 1.

As depicted in FIGS. 1 and 2, in one aspect, the present invention may be used with any endoscope in the market with a mechanical rotatable knob-based control system that comprises an endoscope handle 1, a rubber tubing, also known as the endoscope boot, that connects the endoscope handle with the distal insertion tube 7, a connector cable that interfaces with the electronic monitor 2, buttons that control imaging functionalities 4, a rotatable knob controlling the up/down distal tip deflections of the endoscope 22, a rotatable knob controlling the left/right distal tip deflections of the endoscope 5, a locking switch 6 for the left/right angulation control knob, and a locking switch for the up/down angulation control knob not presently displayed in the figures.

In one aspect, the present invention comprises a first mask with teeth-like protrusions 10 about its outer circumference to engage the self-locking mechanism, a second mask with teeth-like protrusions 9 about its outer circumference to engage the self-locking mechanism, a self-locking mechanism 19 and its housing 67 with its housing cap 11, and a distal arched attachment 14 that rests on top of the plateaued surface of the arched portion of the self-locking assembly housing 67 through the means of nuts and bolts 13. The self-locking mechanism housing and the distal arched attachment are fastened to the endoscope handle 1 through the means of two hook and loop straps 20 and 16 respectively.

Figure 3A:
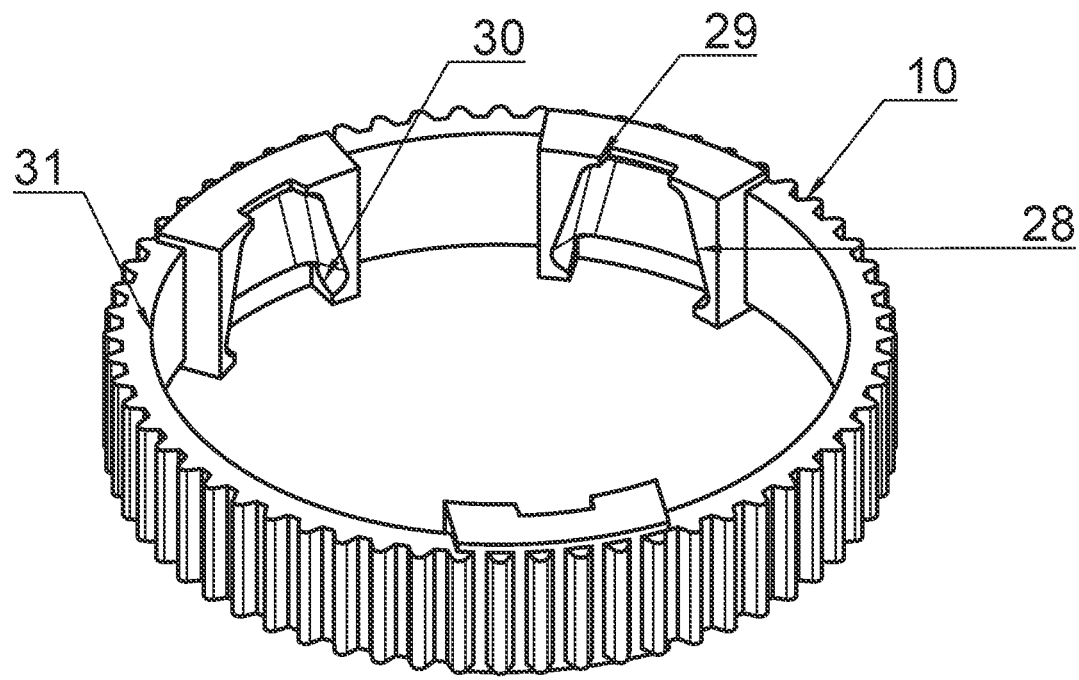
FIGS. 3A and 3B show a perspective view of the left/right and up/down knob masks respectively.
Figure 3B:
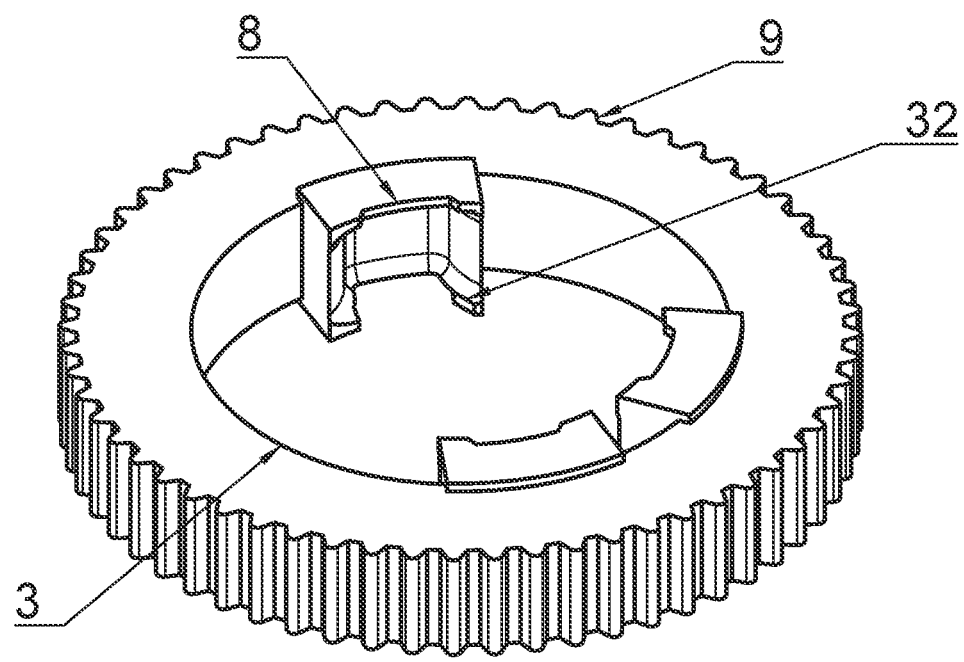

FIG. 3A is an illustration of one aspect of the first mask, which comprises at least one anchor port 29 that mates with protrusions of the up/down angulation control knob 22. The anchor port 29 further comprises a slanted trapezoidal side wall 28 that slides over to mate with the shape of the up/down knob protrusions. The anchor port features an extruded snap-fit interface 30 to allow the anchor ports 29 on the first mask to slide over and lock onto the protrusions of the up/down angulation control knob. The inner edge 31 of the first mask is designed to accommodate space for non-anchored protrusions of the up/down angulation control knob. The first mask, when installed properly, should mate seamlessly with the up/down angulation control knob and rotate in unison. The protrusions 10 along the outer circumference of the first mask serve as both the interface for the hand to rotate the mask and the ratchet teeth for the locking mechanism. Similarly, FIG. 3B illustrates one aspect of the second mask, which also comprises at least one anchor port 8 that mates with the knob protrusion of the left/right angulation control knob 5. The anchor port of the second mask also comprises a snap-fit protrusion interface 32 that allows the left/right knob protrusion to slide into and become secured within the anchor port. The inner edge 3 of the second mask also has a radius to align flush with the remaining unanchored protrusions. The teeth-like protrusions 9 along the outer circumference of the second mask serve a similar function as those for the first mask 10. The teeth-like protrusions 9 and 10 on the first and second knob masks interact with pawls located in the ratchet assembly to achieve the locking function, as depicted in FIGS. 4 and 6.

Figure 4:
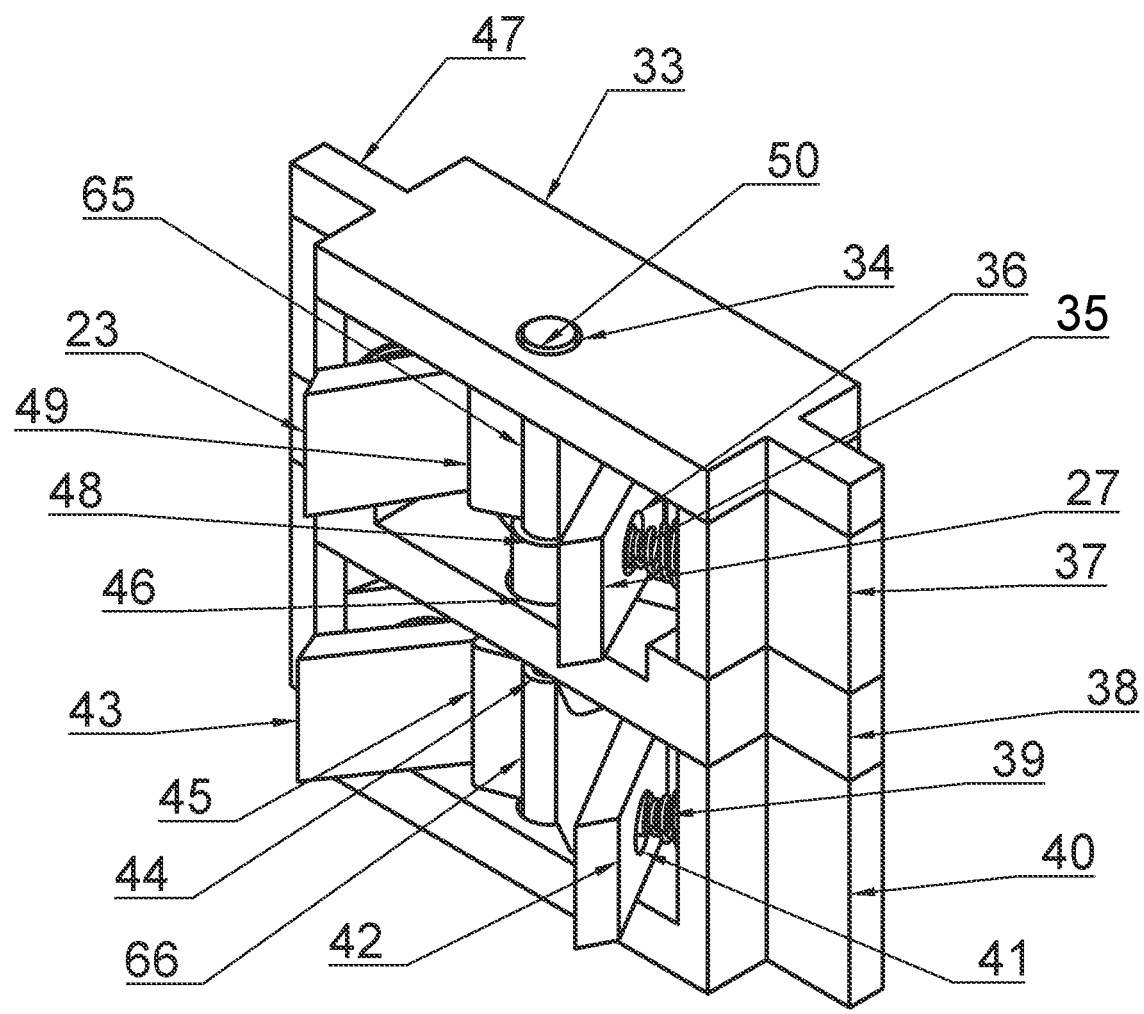
FIG. 4 is a front perspective view of one aspect of the self-locking mechanism assembly
Figure 5:
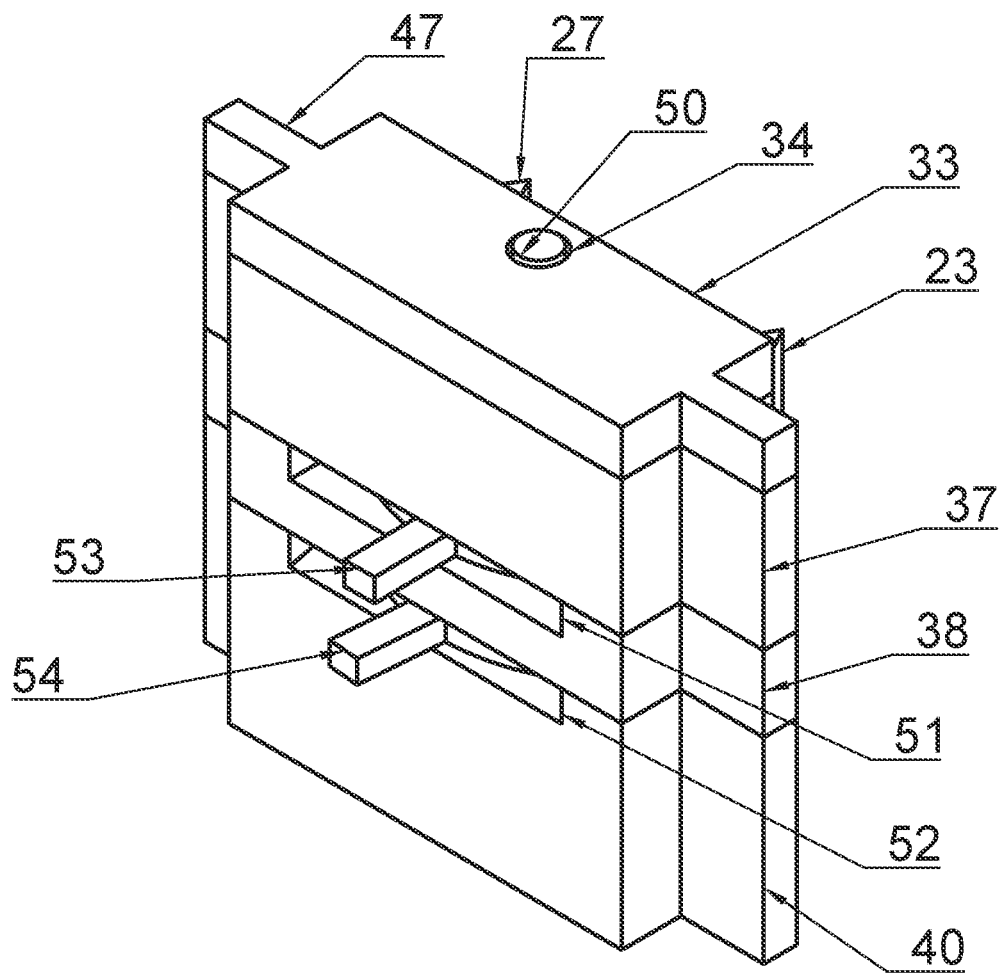
FIG. 5 is a back perspective view of the aspect in FIG. 4 displaying switchable bidirectional toggles.
Figure 6:
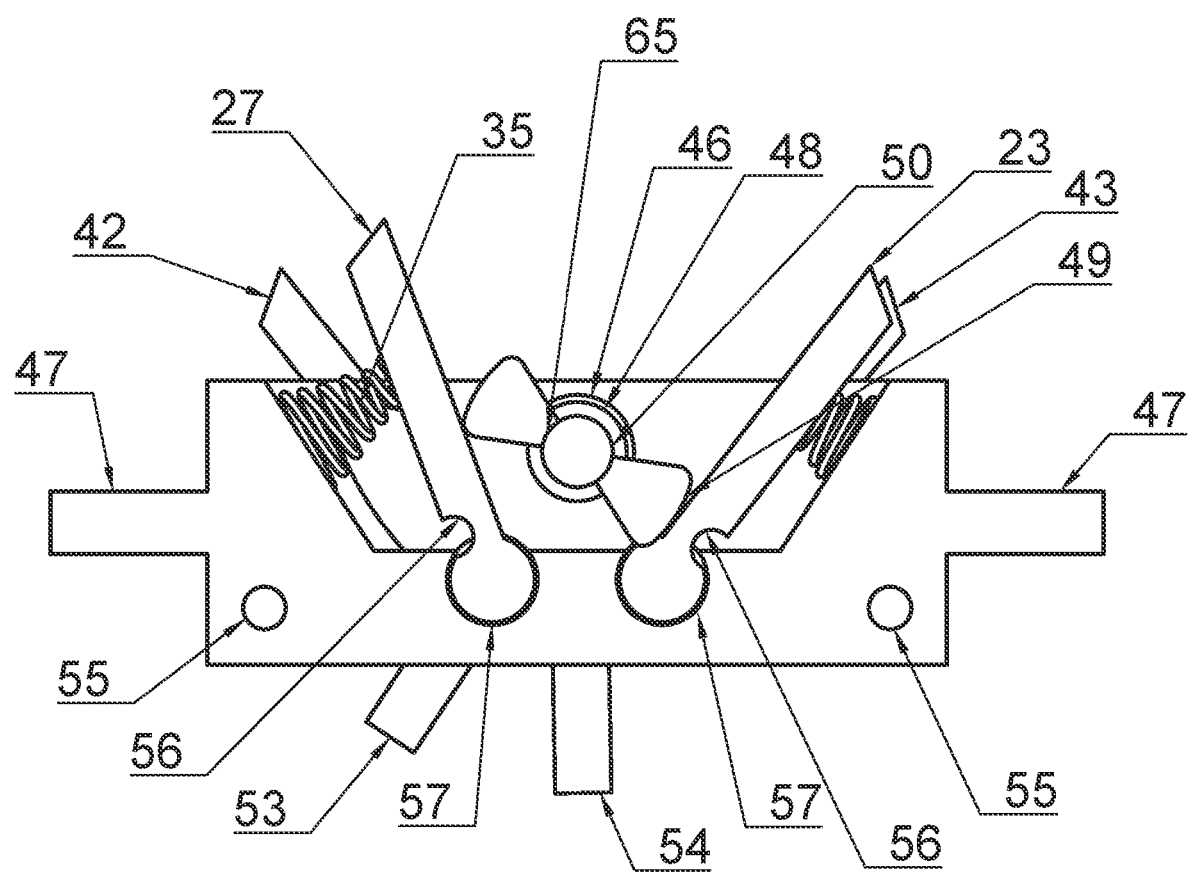
FIG. 6 is a top cross-sectional view of the aspect in FIG. 4 displaying one aspect of the self-locking mechanism.

FIGS. 4-6 illustrate a front perspective view, back perspective view, and a top cross sectional view of one aspect of the self-locking mechanism, respectively. The locking assembly comprises 3 distinct layers (bottom layer 40, middle divider 38, and top layer 37) and a lid 33. The bottom layer further comprises a center cylindrical directional toggle 66, a pawl for locking the clockwise rotation of the first mask while permitting counterclockwise rotation 43, a pawl symmetrically located about the midline of the bottom layer and facing the opposite direction 42 that achieves locking for counterclockwise rotation while permitting clockwise mask rotation, and a compression conical reset spring for each pawl 39 that is fitted within the cavity between the outward side of the pawl 41 and the wall of the bottom layer housing 40. The bottom of the central cylindrical directional toggle 66 is anchored within a centrally located bore in the base of the bottom layer housing 40, and its top is anchored within the lower hollow cylindrical portion of the top cylindrical toggle 48 which has a larger radius to permit the fitting of the bottom cylindrical toggle 66. The bottom cylindrical directional toggle further comprises two pressure-exerting leaflets 45 (one for each pawl) and a rectangular extension arm 53 at the top of the cylindrical piece and extending through the back rectangular slit 52 at the top of the bottom layer housing for the operator to control the toggle states. The top layer 37 follows a similar layout. It comprises a central cylindrical directional toggle 65 with two pressure-exerting leaflets 49 protruding in opposite directions about the center of the cylinder, two self-locking pawls 23 and 27 for locking the second mask in either rotation direction, and a compression conical reset spring 35 for each pawl located between the shallow cavities on the outward side of the pawl 36 and the top layer housing wall. The wider bottom portion of the central directional toggle of the top layer is anchored below through the bore 46 located at the center near the front edge of the middle divider 38. The thinner cylindrical portion 50 of the central directional toggle of the top layer is anchored above through the bore 34 located at the midline towards the front edge of the assembly lid 33. The cylindrical toggle of the top layer also features an extension toggle arm 53 located at the bottom of the cylinder and extends through the back slit 51 of the middle divider. A rectangular protrusion 47 is located symmetrically about the midline at the two far edges of every layer in the self-locking assembly, so that the assembly can slide into the matching cavities 60 within the arch of the self-locking mechanism housing 12, as shown in FIG. 7.

In one aspect, as depicted by FIG. 5, the extension arms 53 and 54 of the two directional control toggles protrude through the back wall of the self-locking assembly, which create an interface for the operator to switch the directional toggle state.

FIG. 6 depicts one aspect of the self-locking mechanism from the top layer of the self-locking assembly. Each of the two pawls of the top layer 23 and 27 comprises a cylindrical portion that acts as the connection interface to the top layer housing 37 by fitting inside a semicircular cavity 57 located within the back wall of the top layer housing. The pawls consist of a long rectangular portion with a slanted tip on its distal end that aligns flush, when activated, with the teeth-like protrusions 9 along the second mask shown in FIG. 3B. A small semicircular cavity 56 near the cylindrical portion of the pawl is used to create more freedom of motion for the pawl to rotate within the semicircular cavity in the top layer housing 57. In one aspect, 3 toggle states can be achieved by switching the directional toggles: clockwise lock, counterclockwise lock, and disengaged. As shown in FIG. 6, the up/down toggle 54 remains in the disengaged state, so the first mask is allowed to freely rotate in either direction. The left/right toggle switch 53 is activated to the counterclockwise lock state so that the corresponding second mask is permitted to rotate clockwise while the counterclockwise direction is prohibited. The mechanism works as follows: when the left/right toggle 53 is activated to the counterclockwise lock state, the central cylindrical rod 50 rotates clockwise about its center axis within the bore of the top layer housing base 46. The two leaflets 49 joined at the middle cylindrical rod 50 in turn rotates clockwise, which exerts pressure on the clockwise locking pawl 23 and pushes it closer to the back wall of the top layer housing. The movement of the leaflets also releases pressure on the counterclockwise locking pawl 27, which allows the compression conical reset spring 35 to activate the counterclockwise locking pawl by restoring the reset spring's resting length and pushing the pawl towards the central cylindrical rod 50 of the left/right toggle. Turning the directional toggle 53 to the opposite direction would result in the opposite mechanism to achieve a clockwise locking state. The directional toggle mechanism of the bottom layer for the up/down knob mask functions in the same fashion. In FIG. 6, two protrusions 55 seen in the back corners of the top layer housing are located ubiquitously on every layer of the locking assembly, which would fit inside matching bores on the bottom of each layer to align all the layers in the assembly.

Figure 7:
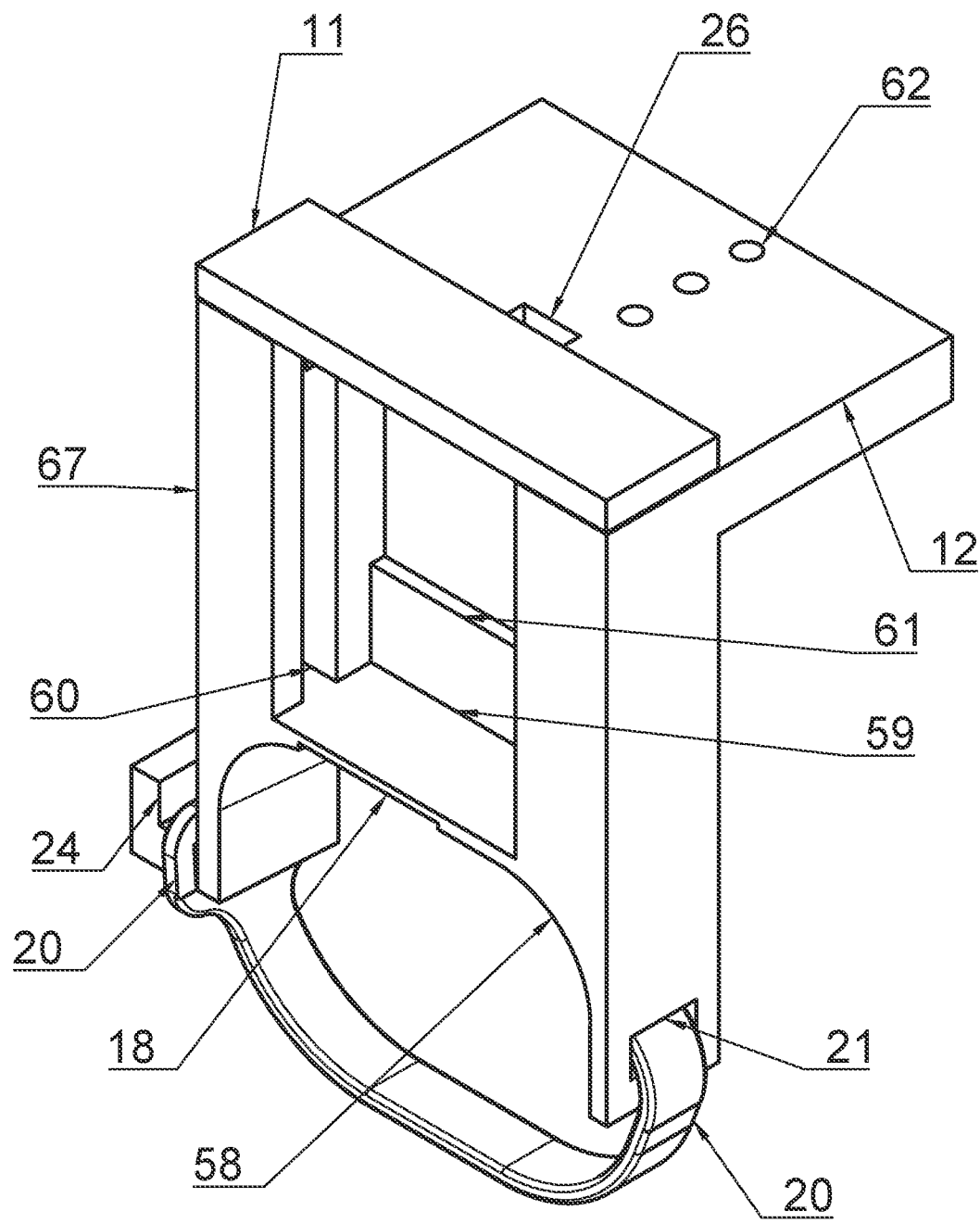
FIG. 7 is a perspective view of one aspect of the housing unit for the self-locking mechanism assembly and the fastening strap.

FIG. 7 displays one aspect of the housing for the self-locking assembly. The base of the housing 59 provides a flat platform to rest the bottom layer of the self-locking assembly, and the backboard of the housing 61 provides extra security for the self-locking assembly. A rectangular cavity runs along both side walls to create a slit to slide in the rectangular protrusions 47 along both ends of the self-locking assembly to secure the self-locking assembly within the housing. The housing lid 11 completely seals and locks in the self-locking assembly from the top. A small rectangular slit is located on the proximal end of the overhang portion of the assembly housing to allow for the locking assembly with the protruding toggles 53 and 54 to slide into the housing without obstructions. The overhang portion of the housing 12 with three bores 62 are used in conjunction with nuts and bolts to connect the distal arched attachment 14 to provide structural stability to the present invention. The locking assembly housing further comprises features that can be attached to the endoscope handle 1: a curved bottom surface 58 that is fitted around the natural curvature of the endoscope handle 1, a thin slit 18 along the bottom surface to accommodate the protrusions along the length of the endoscope handle not presently shown in the drawings, and an anchor hook 24 and an feeding loop for the hook and loop strap 20, which is used in one aspect to fasten and secure the housing onto the endoscope handle.

Figure 8:
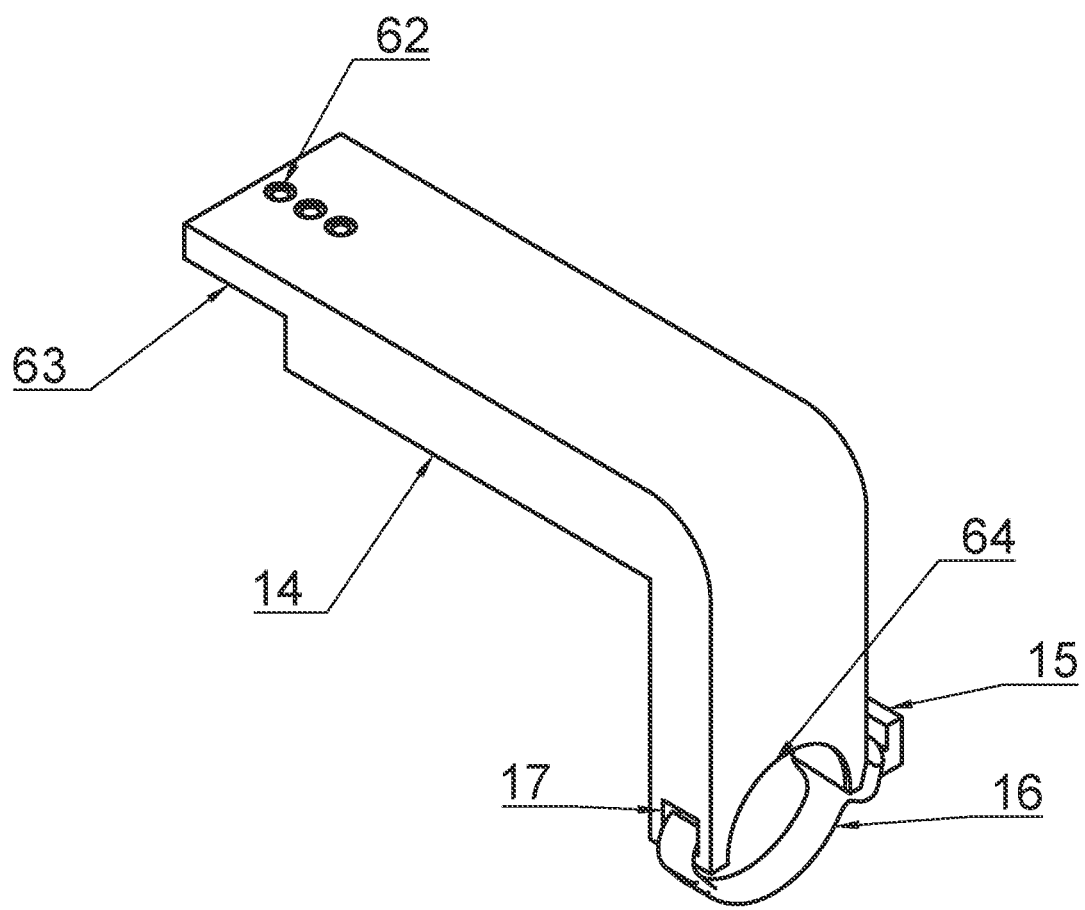
FIG. 8 is a perspective view of one aspect of the arch attachment and its fastening strap.

FIG. 8 illustrates one aspect of the arched arch attachment 14, which further secures the attachment apparatus onto the handle of the endoscope while allowing the operator's hand to grasp the endoscope handle 1. The arch attachment comprises a thin overhang portion 63 that interfaces with the overhang of the self-locking assembly housing 12 and can be connected and secured through the three bores 62 with nuts and bolts 13. The arch attachment further comprises a fastener onto the distal portion of the endoscope handle 7, a curved bottom surface 64 that is fitted to the curvature of the distal portion of the endoscope handle, a anchor hook 15 and feeding loop 17 for a hook and loop strap 16 to be fastened around the endoscope handle, similar to that of the locking assembly housing 20.

In one aspect, the self-locking assembly is assembled in a layer-by-layer fashion starting from the bottom layer 40. The central cylindrical part of directional toggle 44 is positioned inside the bore on the base of the bottom layer, and the two pawls 42 and 43 are then positioned into the two semicircular cavities 57 inside the wall of the bottom layer housing. The pawls are arranged so that the shallow cavity 41 for the conical reset spring is oriented toward the back of the bottom layer housing. The two compression conical reset springs 39 for the bottom layer are then placed between the pawl and the side wall of the bottom layer housing to complete the assembly of the bottom layer. The middle divider 38 is then placed on top of the bottom layer, followed by the positioning of the top layer housing 37 on top of the middle divider. The central cylindrical directional toggle 65, the two pawls 23 and 27, and the two compression conical reset springs 35 for the top layer are then assembled in the same fashion and sequence as the bottom layer. After the assembly of the top layer is completed, the assembly lid 33 is placed on top of the top layer housing by aligning the protrusions 55 and the matching holes. It should be noted that in a clinical setting, the self-locking assembly should be pre-assembled to reduce the total installation time.

In one aspect, the present invention is assembled by first installing the first mask by sliding the mask over the up/down endoscope knob 22 until protrusions of the knob snaps into position over the snap-fit protrusion interface 30 into the anchor ports 29. The second mask is installed in the same fashion onto the left/right endoscope knob 5. The housing of the self-locking assembly 67 is assembled next by first positioning the housing upright with the bottom surface of the housing's arch 58 flush against the endoscope handle 1 near the distal end of the handle, with the arched plateau portion of the housing 12 pointing to the distal end of the endoscope. Then, the housing proximally is slid towards the angulation control knobs until the housing can no longer move due to the widening of the endoscope handle. A hook and loop strap 20 is then secured onto the anchor hook 24 and fed through the feeding loop 21 before doubling back and tightened. Once the housing is secure, the pre-assembled self-locking assembly is then slid into the central cavity of the housing by placing the rectangular protrusions 47 that run along both sides of the locking assembly into the matching rectangular cavities 60 along both sides of the housing wall. It should be noted that both toggle protrusion arms 53 and 54 should be in the disengaged state to slide through the rectangular opening 26 on the plateau portion of the locking assembly housing. The locking assembly is secured within the housing by sealing with the housing lid 11. The arched handle attachment 14 is assembled by aligning the distal curved bottom surface 64 flush against the surface of the endoscope boot 7, while ensuring that the three through-holes 62 align with those on the plateaued portion of the self-locking assembly housing 12. The distal end is fastened in a similar fashion as the locking assembly housing by anchoring a hook and loop strap 16 on the anchor hook 15 and feeding through the feeding loop 17 and tightened. Finally, nuts and bolts 63 are used to connect and secure the arched handle attachment together with the locking mechanism housing.

To take device weight and sterilizability into consideration, one aspect of the invention can be made by using medical-grade sterilizable plastics such as Polyether Ether Ketone (PEEK) plastic, which is lightweight and durable. The nuts and bolts and compression conical reset springs (35) in one aspect can be made using stainless steel.

In one aspect, the present invention comprises a detent-based self-locking mechanism.

Figure 9:
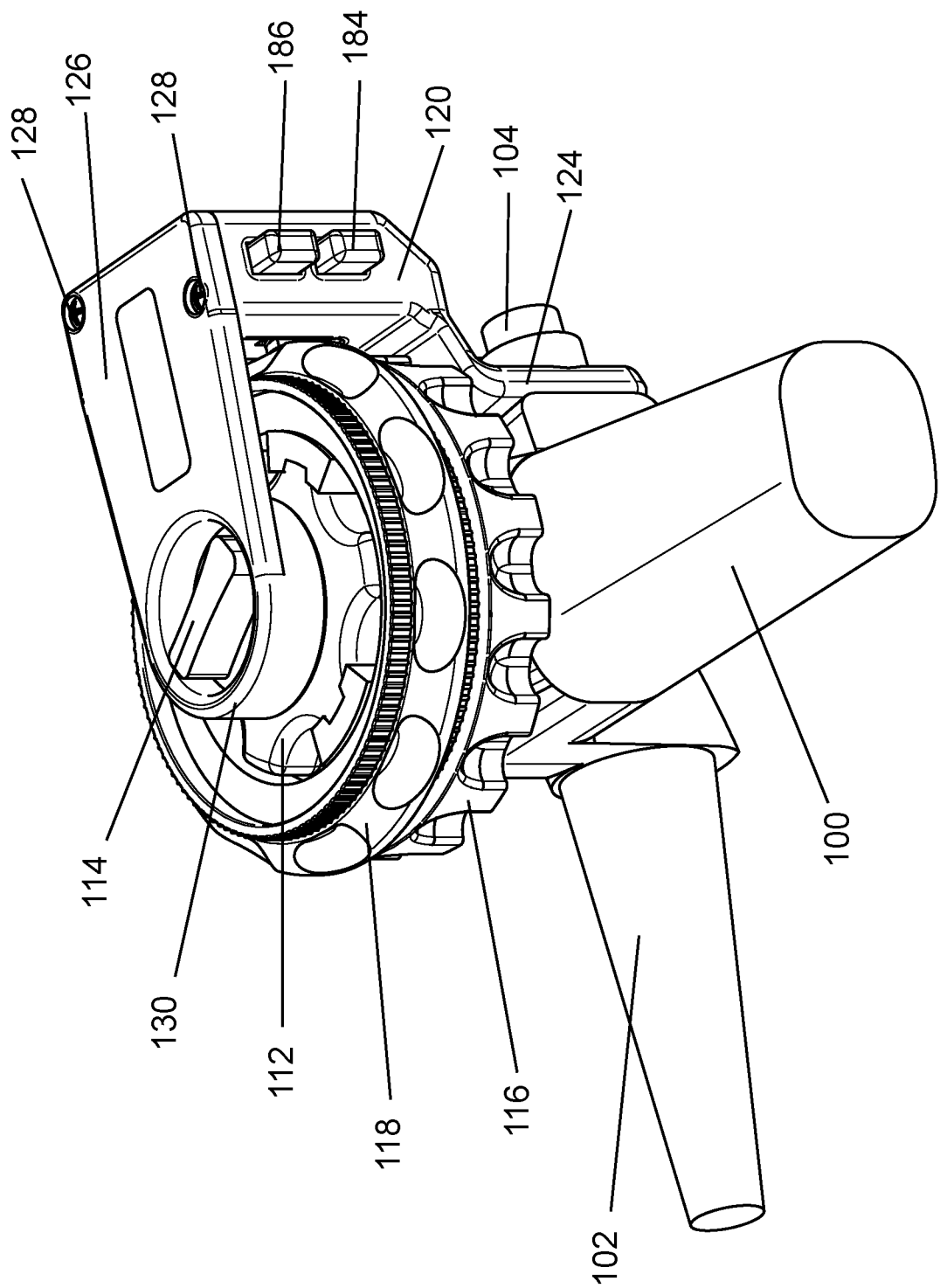
FIG. 9 is an isometric perspective view of one aspect of the present invention installed onto the endoscope handle.
Figure 10:
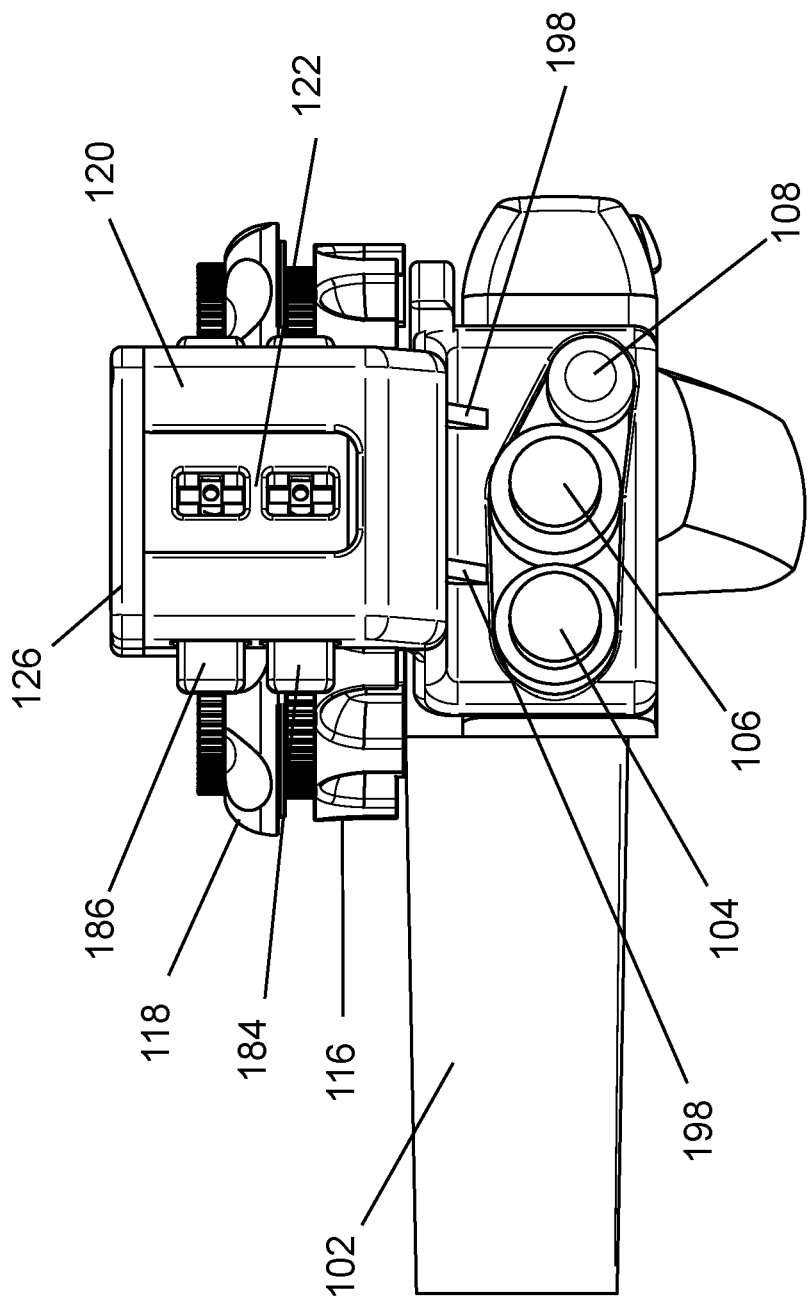
FIG. 10 is a back perspective view of the aspect displayed in FIG. 1.
Figure 11:
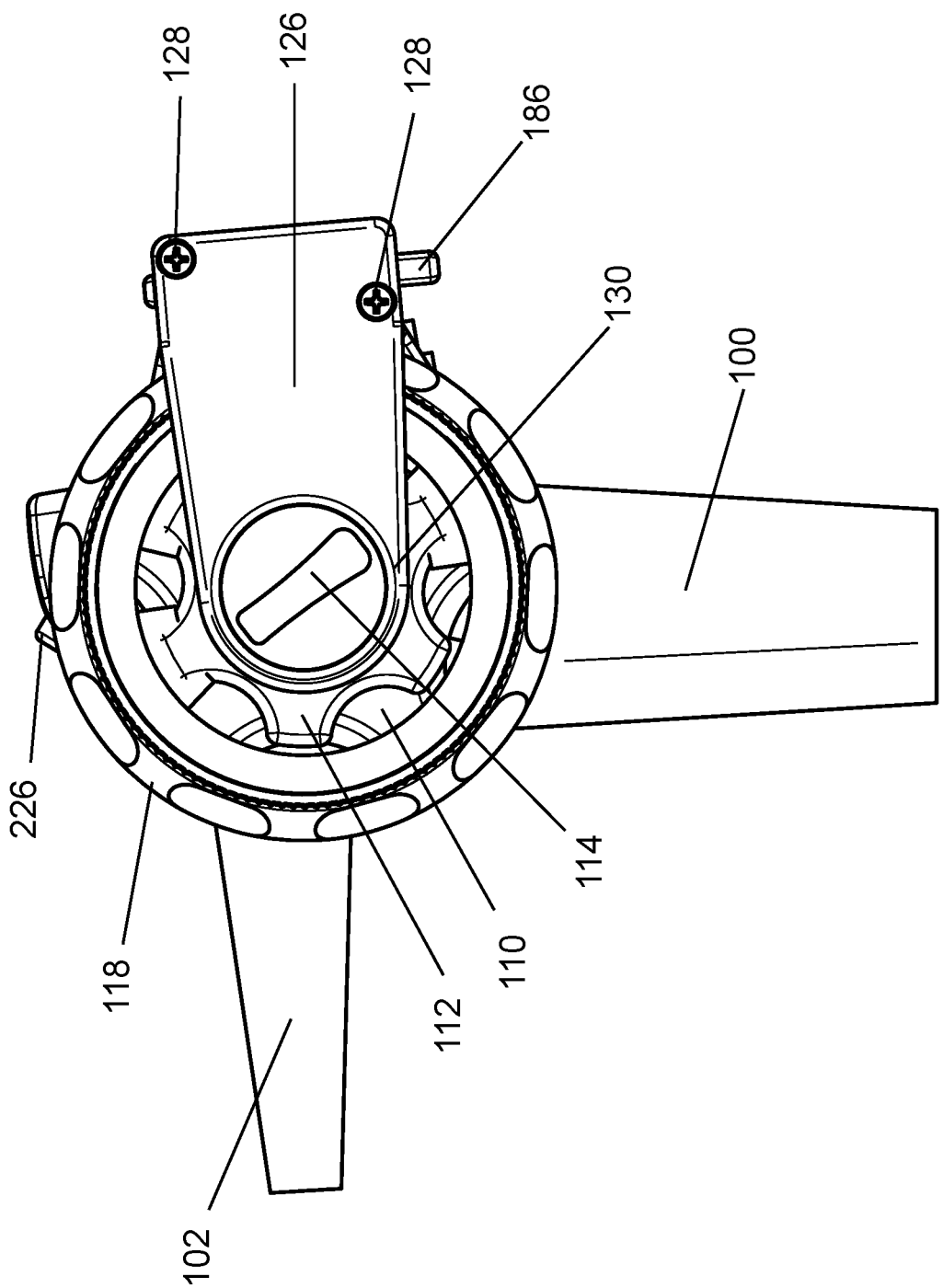
FIG. 11 is a top perspective view of the aspect displayed in FIG. 1.
Figure 12:
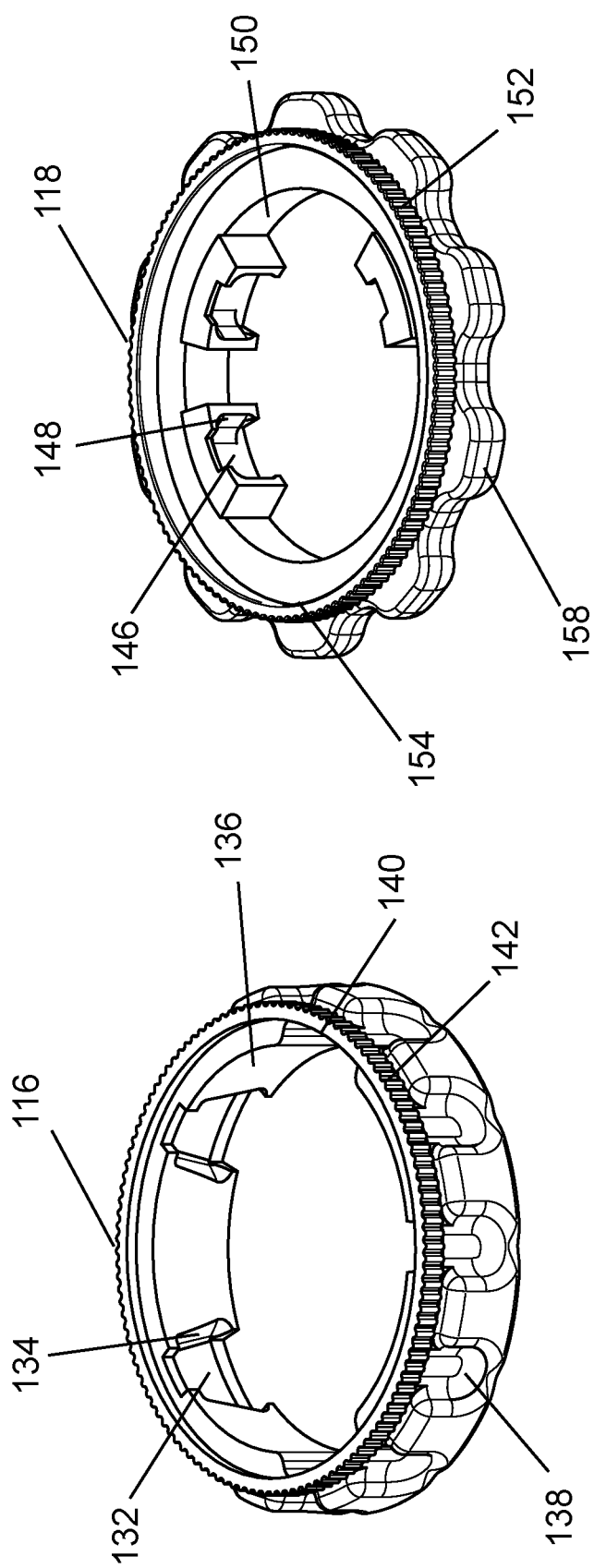
FIGS. 12A and 12B show an isometric perspective view of the up/down and left/right knob masks respectively.

As depicted in FIGS. 9, 10, and 11, one aspect may be used with any endoscopes in the market with a mechanical rotatable knob-based control system that comprises an endoscope handle 100, a connector cable that interfaces with the electronic monitor 102, endoscope buttons comprising an air/water flushing valve 104, a suction valve 106, and an imaging remote switch 108, a rotatable knob controlling the up/down distal tip deflections of the endoscope 110, a rotatable knob controlling the left/right distal tip deflections of the endoscope 112, a locking switch 114 for the left/right knob, and a locking switch for the up/down knob not presently displayed in the illustrations.

FIGS. 9, 10, and 11 are illustrations of the full assembly of one aspect of the present invention. The full assembly comprises a first mask 116 that mates with the up/down angulation control knob of the endoscope and a second mask 118 that mates with the left/right angulation control knob, a self-locking mechanism housing body 120 housing an internal self-locking mechanism 122 and a connected endoscope button locking hoop 124 that is anchored to the endoscope buttons 104, 106, and 108, and a housing lid 126 anchored by screws 128 to the housing body 120, the housing lid further comprising a circular locking hoop 130 to anchor the device onto the left/right angulation knob lock.

Figure 16:
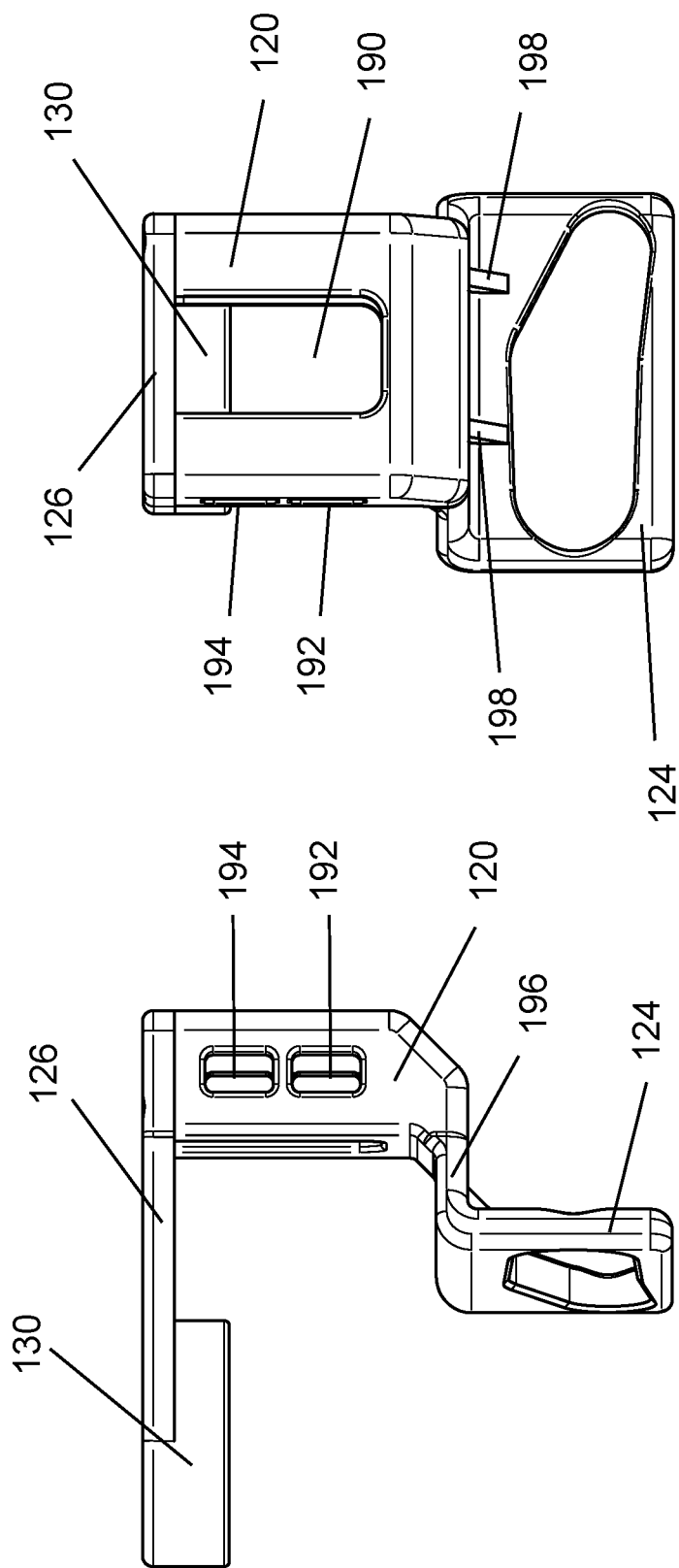
FIGS. 16A and 16B are side and back perspective views of one aspect of the attachment housing body and its housing lid for the self-locking mechanism.
Figure 17:
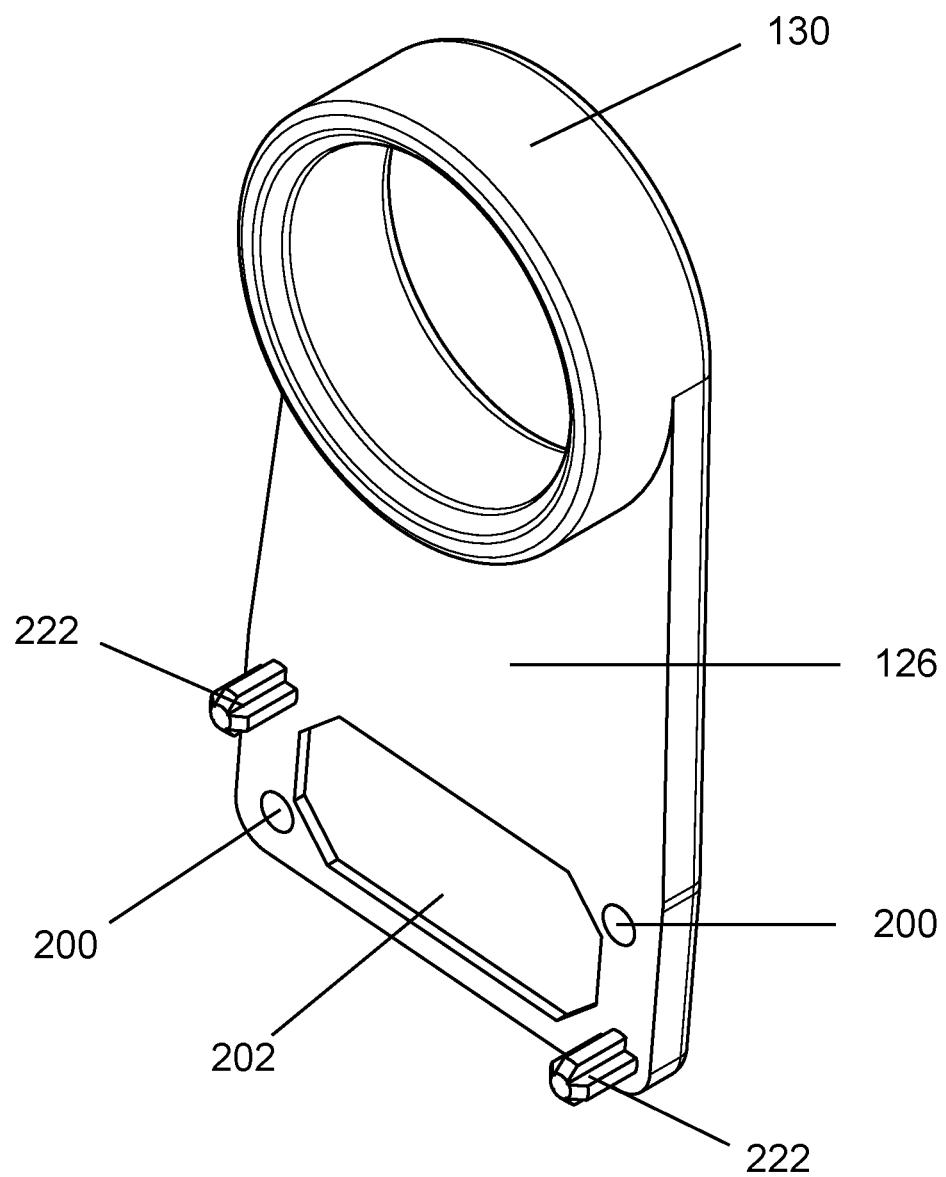
FIG. 17 is an isometric view of the housing lid displayed in FIGS. 16A and 16B.

FIG. 12A is an illustration of one aspect of the first mask 116, which comprises at least one anchor port 132 that mates with protrusions of the up/down angulation control knob 110. The anchor port 132 further comprises a slanted trapezoidal side wall 134 that slides over to mate with the contour of the up/down knob protrusion. The anchor port 132 features a snap-fit interface 134 to the first mask 116 to slide over and lock onto protrusions of the up/down angulation control knob 110. The inner edge 136 of the first mask 116 is designed to accommodate space for non-anchored protrusions of the up/down angulation control knob 110. The first mask 116, when installed properly, should mate seamlessly with the up/down angulation control knob 110 and rotate in unison with one another. The first mask 116 also comprises an interface 138 on its outer circumference that provides a surface for the first mask 116 to be manipulated. The teeth-like protrusions 142 along the outer circumference of the teeth ring 140 that is fixed on top of the first mask 116 serve as locking teeth 142 for the locking mechanism. The teeth-like protrusions 142 on the first mask 116 interact with detent pistons 144 located in the self-locking mechanism to achieve the locking function, as depicted in FIGS. 16 and 17. The depression between each two teeth-like protrusions define discrete locking positions along the circumference of the first mask 116, which offers stable and accurate operation for controlling the endoscope distal tip. The teeth-like protrusions 142 can be made more numerous with a finer size to further allow finer controls.

As depicted in FIG. 12B, one aspect of the second mask also comprises one or more anchor ports 146 that mates with knob protrusions of the left/right angulation control knob 112. The anchor port 146 of the second mask 118 also comprises a snap-fit interface 148 that allows the left/right knob protrusion to slide into and be secured within the anchor port 146. The inner edge 150 of the second mask 118 also has a radius to align flush with the remaining unanchored protrusions. The teeth-like protrusions 152 along the outer circumference of the teeth ring 154 that is fixed on the top surface of the second mask 118 also serve a locking function by interacting with a detent piston 156 on the self-locking mechanism. The second mask 118 also contains an interface 158 on its outer circumference that provides a surface for the second mask 118 to be manipulated.

Figure 13:
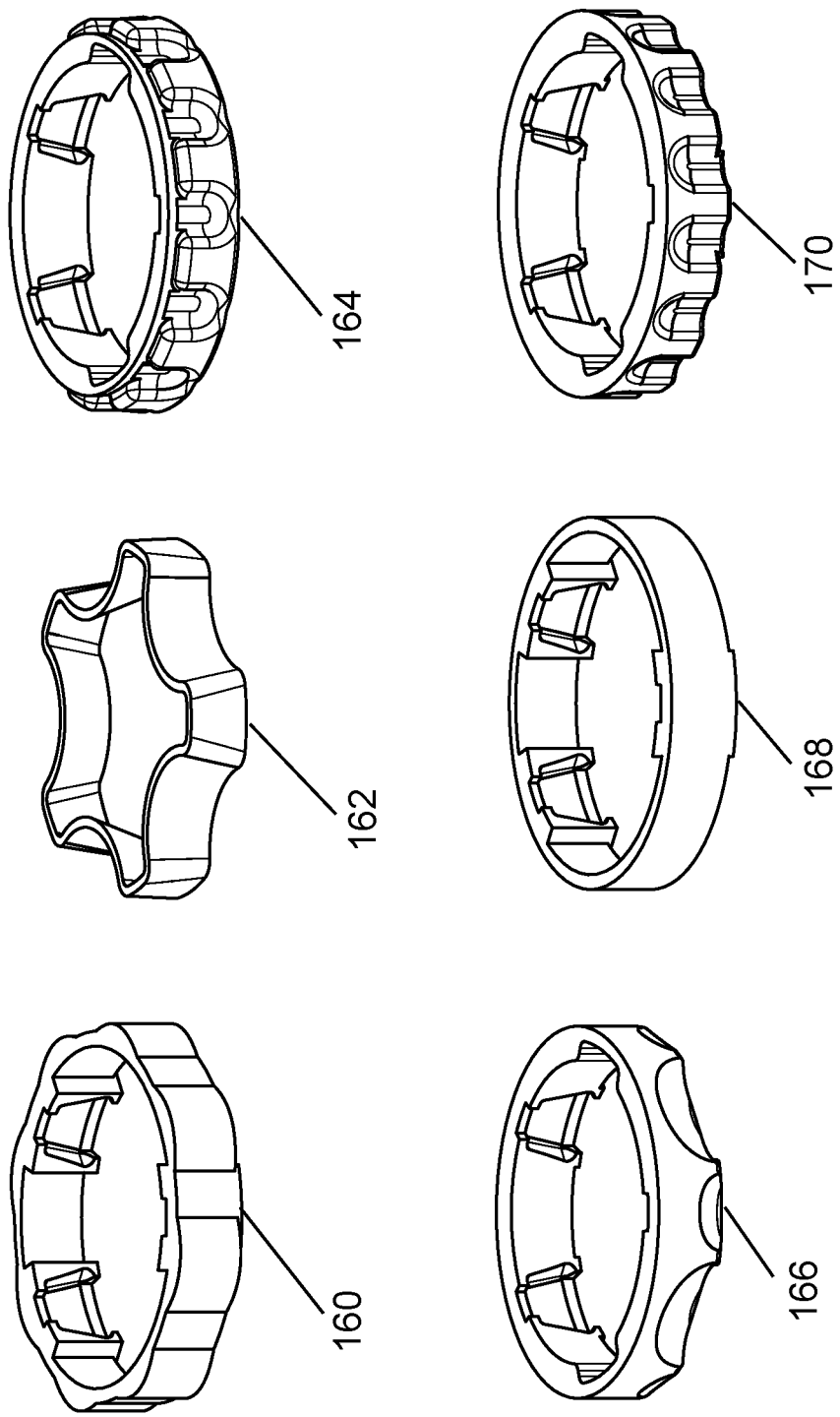
FIG. 13 is an isometric perspective view of six alternative aspects of the left/right knob masks.
Figure 14:
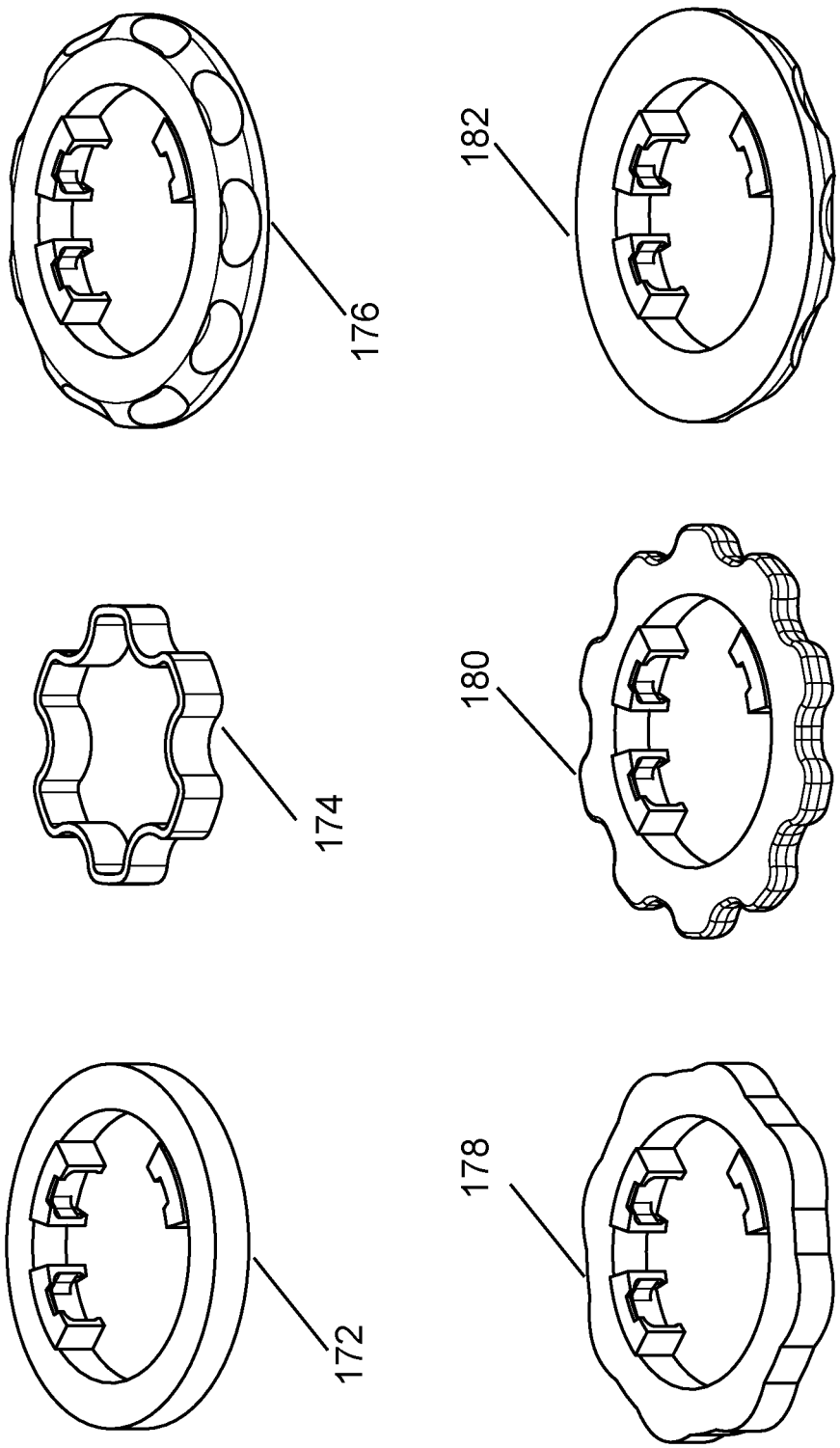
FIG. 14 is an isometric perspective view of six alternative aspects of the up/down knob masks.

FIGS. 13 and 14 illustrate one aspect of the knob masks within the attachment apparatus kit, which comprises six different interfaces 138 on the outer surface of the first mask and those of the second mask 158, respectively. The interfaces 138 and 158 are located on the outer circumference of the knob masks to provide a surface for endoscope angulation control knob manipulation. These interfaces are designed to fit individual sizing and shape preferences and offer customizability in the control interface for the users to maximize user comfort and ergonomics.

One aspect of the interfaces 138 for the first mask 116 consist of but are not limited to a thumb-sized groove 160, an endoscope knob-shaped extension 162, a top-facing teardrop-shaped interface 164, a scallop-shaped grooved interface 166, a smooth surface interface 168, and a bottom-facing teardrop-shaped design 170. One aspect of the interfaces for the second mask 118 consist of but are not limited to a smooth surface interface 172, a left/right endoscope knob-shaped extension 174, a top-facing scallop-shaped grooved interface 176, a thumb-sized groove 178, a flower petal-shaped interface 180, and a bottom-facing scallop-shaped groove interface 182.

Figure 15:
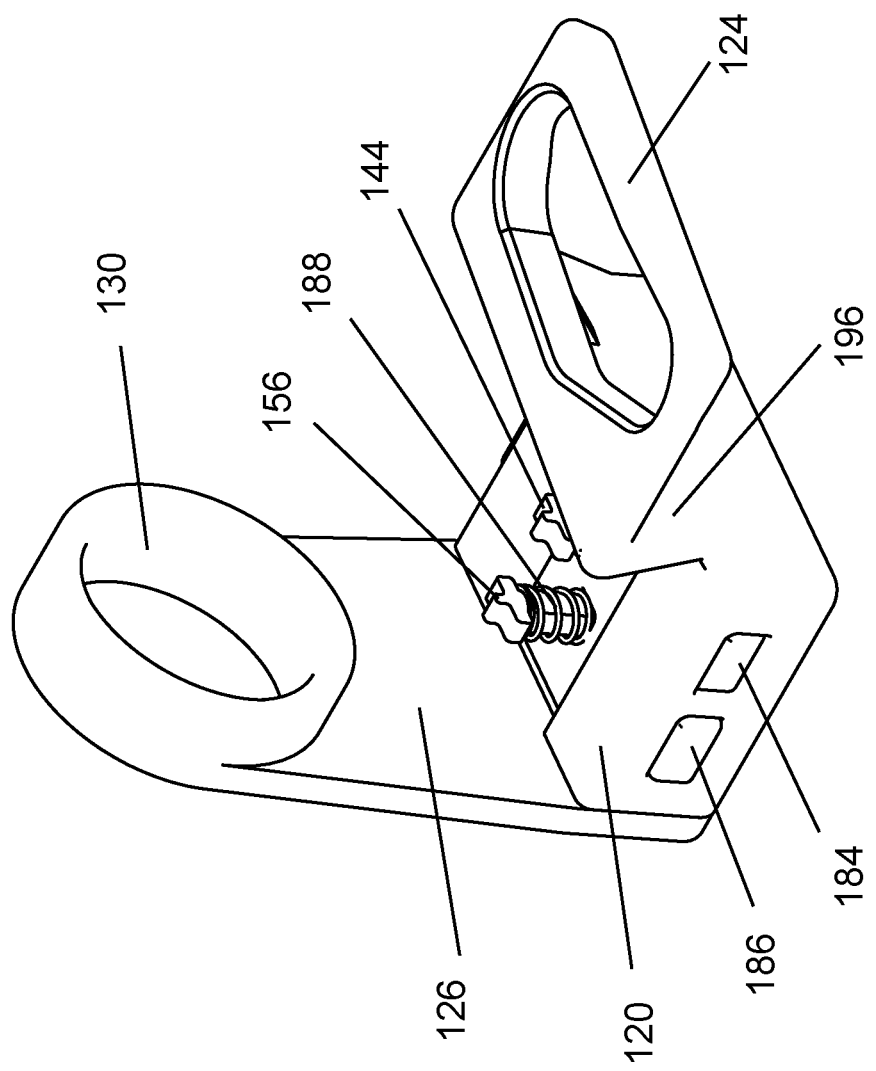
FIG. 15 is an isometric perspective view of one aspect of the self-locking mechanism assembly resting within its housing.

FIG. 15 is an illustration of one aspect of the full self-locking assembly, which comprises a housing body 120 that is enjoined by an endoscope button locking hoop 124, and a housing lid 126 with a circular locking hoop 130. The housing body 120 comprises a self-locking mechanism 122 with a first toggle 184, a second toggle 186, a first detent piston 144 and spring 188, and a second detent piston 156 and spring. When the full assembly is secured onto the endoscope control handle 1, with the button locking hoop 124 fastened around the endoscope buttons and the circular locking hoop 130 secured around the left/right endoscope knob locking switch 114, the detent pistons 144, 156 engage with the teeth-like protrusions of the first 116 and second masks 118, respectively, to lock the knob masks in place as they are turned.

FIGS. 16A and 16B are illustrations of the side perspective and back perspective views of one aspect of the locking mechanism housing body 120 and its housing lid 126. The housing body 120 further comprises a housing cavity 190 for the self-locking mechanism 122, a first toggle cavity 192 for a first toggle 184, a second toggle cavity 194 for a second toggle 186, and a plateaued bridge 196 that connects the housing body 120 with the button hoop 124, and support bridges 198 that strengthens the structural integrity of the connection between the plateaued bridge 196 and the endoscope button hoop 124.

FIG. 17 is an isometric perspective view of one aspect of the housing lid 126. As depicted, the housing lid 126 comprises a circular locking hoop 130 for anchoring the device onto the left/right endoscope knob lock 114, alignment pins that align the housing lid 126 and the housing body 120 for increased ease of assembly, screw holes 200, that allow locking of the housing lid 126 onto the housing body 120, and a locking cage depression 202 to fix a locking cage in place for device stability.

Figure 18:
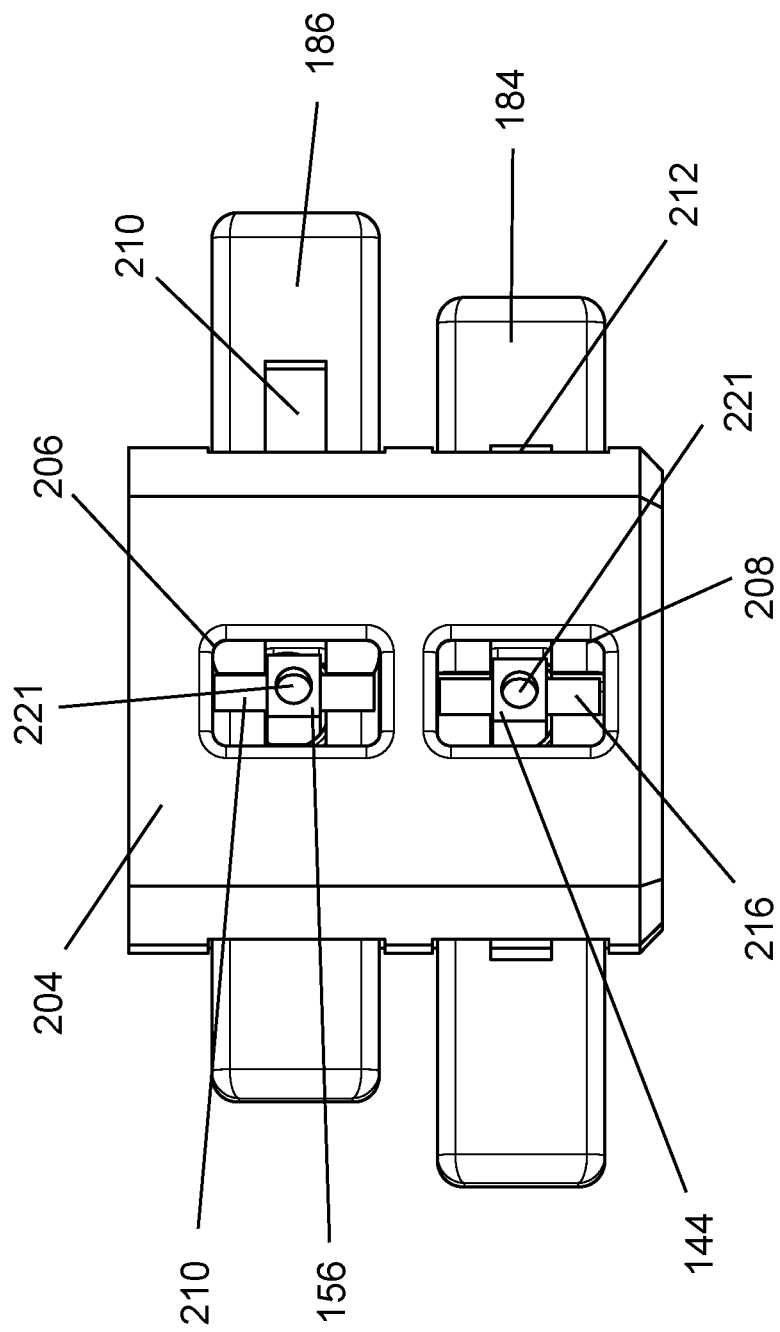
FIG. 18 is a back perspective view of the self-locking mechanism assembly.

FIGS. 18 and 19 are the back and top perspective views of one aspect of a locking cage housing 204 of the self-locking mechanism 122, respectively. The cage housing 204 comprises a bottom cavity 208 to house the bottom toggle 184 as well as its respective first detent piston 144 and a top cavity 206 to house the top toggle 186 and its respective second detent piston 156. The bottom and top toggles each have an opening slit within its center, 210 and 212, respectively, that create a space to house the first and second detent pistons, 144 and 156, respectively. These detent pistons are secured flush against the bottom toggle 184 and top toggle 186 with catch pins 216 and 214, respectively. Finally, the first detent piston 144 and second detent piston 156 communicate with their own respective detent springs 188 (first detent piston spring not pictured), which push against their respective toggles on one end 184 and 186 and the head of their respective detent pistons on the other, which pushes the detent pistons forward to engage the locking teeth of the second mask 118 and the first mask 116, respectively. The push of the detent springs are limited by the bottom and top catch pins 216 and 214, respectively, by catching against the walls of their respective toggles 184 and 186, respectively.

Figure 19B:
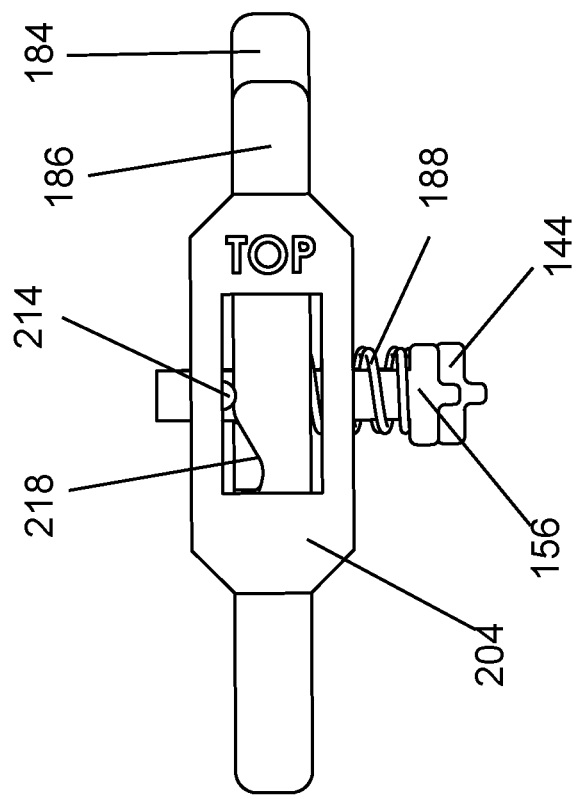
FIGS. 19A and 19B are top perspective views of the engaged state and disengaged state of one aspect of the self-locking mechanism, respectively.
Figure 19A:
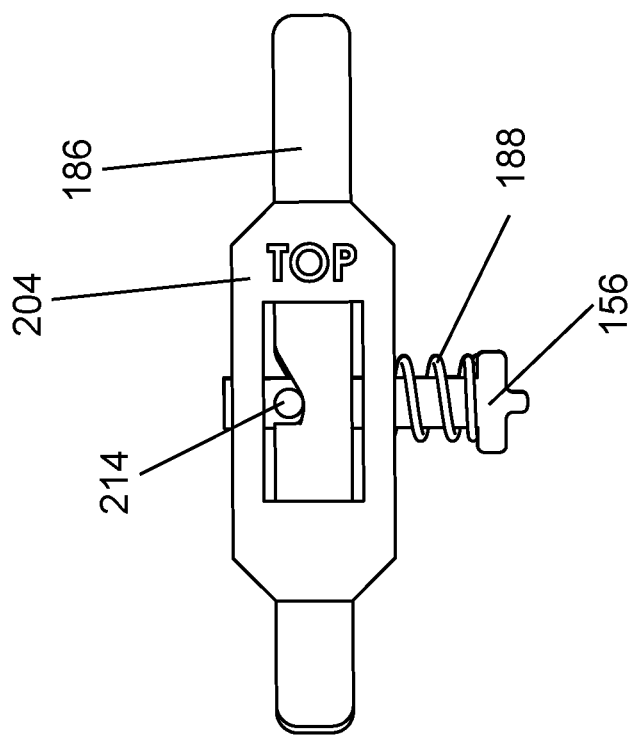

FIG. 19A and 19B illustrate the engagement and the disengagement of the second detent piston 156 and its communication with its respective detent spring 188 and top toggle 186, respectively. When the top toggle 186 or bottom toggle 184 is pushed toward the side, their respective catch pins 214 and 216 slide out of the toggle divot 218 along a slanted edge, pulling their respective detent pistons 156 and 144 back and compressing their respective spring 188 in order to disengage the respective detent piston 156 and 144 from its forward position.

Figure 20:
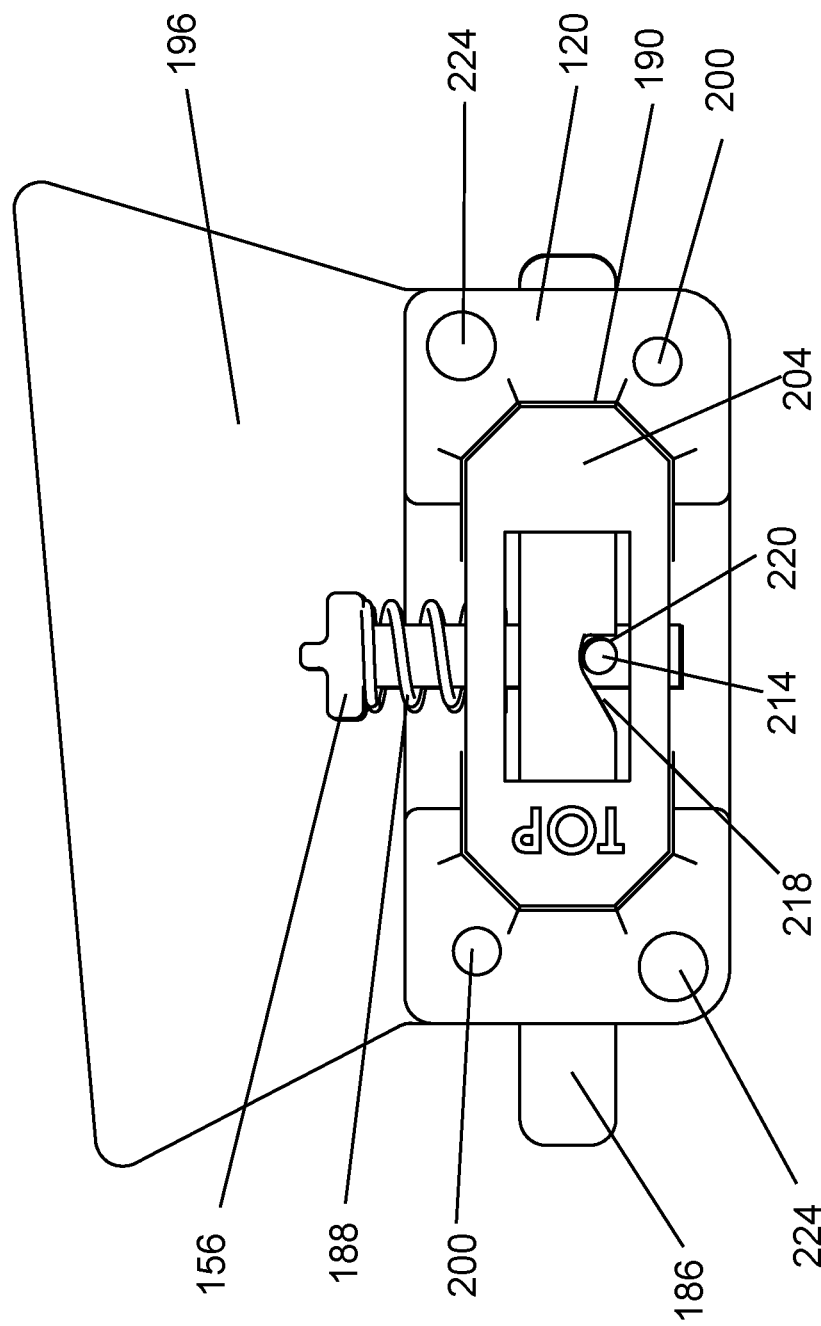
FIG. 20 is a top perspective view of the self-locking mechanism resting within its housing attachment body.

FIG. 20 is a top view of one aspect of the housing cage 204 of the self-locking mechanism resting within the housing body 120 of the apparatus. The cage housing 204 of the self-locking mechanism has an octagonal shape that matches the housing cavity 190 in the housing body 120, allowing the cage housing 204 to align flush within the corresponding housing cavity 190 on the housing body 120. In the illustration, the locking mechanism can be observed in its engaged state, as the top catch pin 214 of the second detent piston 156 is resting in the toggle divot 218, allowing the compression spring 188 to push the head of the second detent piston 156 forward to engage the teeth-like protrusions 152 of the corresponding second knob mask 118. In addition, screw holes 200 and pinholes 224 can be observed in the four corners of the housing body 120 for the locking screws and alignment pins on the housing lid 126 to be installed.

In one aspect, the attachment apparatus kit is assembled by installing the first mask 116 by sliding the mask over the up/down endoscope knob 110 until its anchor ports 132 snap over the protrusions of the up/down endoscope knob 110. Similarly, the second mask 118 is installed by sliding the mask over the left/right endoscope knob 112 until its anchor ports 146 snaps over the protrusions of the left/right endoscope knob 112. The self-locking mechanism housing cage 204 is slid snugly into the cavity 190 of the housing body 120 of the attachment apparatus, ensuring that the top and bottom toggle cavities 206 and 208 for the top and bottom toggles 186 and 184 align with the top and bottom toggle cavities 194 and 192 of the housing body 120 of the attachment apparatus. Once the housing cage 204 for the locking mechanism is securely nested inside the housing body 120 of the attachment apparatus, the bottom toggle 184 is slid into the bottom cavities 192 of the housing body 120 of the attachment apparatus and the housing cage 204 for the locking mechanism. Then, the first detent piston 144 is wrapped with a spring and inserted with its smaller end through the center slit 212 in the bottom toggle 184. The spring of the first detent piston 144 is compressed against the wall of the housing cage 204 until it reveals a through-hole 220 for the insertion and securing of the catch pin 216 in the bottom toggle divot 218. A set screw can be installed on the set screw hole 221 at the tail of the first detent piston 144 to further secure the catch pin in place. The top toggle 186 is then slid into the top cavities of the housing body of the attachment apparatus 194 and the housing cage for the locking mechanism 194, similar to the bottom toggle 184.

Then, the second detent piston 156 is wrapped with a detent spring 188 and inserted with its smaller end through the center slit in the top toggle 210. The detent spring 188 is compressed against the wall of the housing cage 204 until it reveals the through-hole 220 for the top catch pin 214, which is then inserted through the through-hole 220 and secured in the toggle divot 218 of the top toggle. Another set screw can be inserted in the set screw hole 221 for further stabilization. Then, the button hoop fastener 124 is slid over the buttons of the endoscope 104, 106, and 108 to secure the housing body 120 of the apparatus to the endoscope. Then, the top housing lid 126 is aligned to the housing body of the apparatus 120 using the housing lid's alignment pins 220 which slide into matching pin holes in the housing body 224, and the circular hoop fastener 130 is slid securely over the left/right knob locking switch 114. Finally, the top housing lid of the attachment apparatus 126 is secured to the housing body 120 by the use of screws 128.

It should be noted that the present invention only discloses a small number of different aspects that should be covered within the claims of the present invention. For example, one aspect of the self-locking mechanism 122 is a mechanical ratcheting system toggled by lever toggles 53 and 54 to switch locking directions, another aspect of the self-locking mechanism 122 can include a sliding toggle switch that toggles locking direction as the user turns the knob mask one direction or the other. Alternatively, in one aspect, the ratchet system can also include electrical means to achieve locking. In one aspect, the self-locking mechanism 122 is a mechanical detent-based locking mechanism with detent pistons 144 and 156 and compression springs 188. Alternatively, in one aspect, the detent locking can be achieved with a semi-rigid plastic or rubber flipper that engages with the teeth-like protrusions 142 and 152 on the knob masks. In yet another aspect, the detent locking can be achieved through electrical means with magnets and stepper motors.

In one aspect, a different attachment mechanism can be used to secure the housing and the arched handle 14 together such as a snap-fit mechanism. The hook and loop attachment mechanism in one aspect can be replaced by a clamping mechanism to secure the locking assembly housing 67 and arch attachment 14 onto the endoscope handle. One aspect of a fastener of the attachment apparatus is represented by the circular hoop fastener 130 for the left/right knob lock 114 and the button hoop fastener 124 for the endoscope buttons 104, 106, and 108 of the endoscope. Alternatively, the fastening locations can include but are not limited to: a fastener for the up/down knob lock (not pictured), a fastener for the imaging buttons 226 located on the tip of the endoscope, and a fastener for the electrical connector cord 102. One aspect of the attachment methods uses friction as a means of fastening the attachment apparatus to the endoscope. Alternatively, a clamping mechanism similar to the C-clamp, which uses a screw-tightening mechanism that closes in and secures the attachment apparatus to the endoscope, can be used. In another aspect, a clamp similar to a bike seat clamp, which uses a lever that tightens when pushed, can be used to secure the attachment apparatus snug against the endoscope. In yet another aspect, a snap-fit design that snaps two pieces of the attachment apparatus around the endoscope can be used to fasten the attachment onto the endoscope.

In one aspect, the present invention comprises an attachment apparatus kit for modifying an endoscope by mechanically assisting the operation endoscope angulation control knobs, said apparatus comprising:

(a) a pair of knob masks, each configured to mount onto an endoscope angulation control knob, the masks, comprising: teeth-like protrusions around their outer circumferences;

(b) a self-locking mechanism, comprising: two pairs of pawl members, the paired pawl members being adjacent to another member and each pawl member being configured to communicate with the teeth-like protrusions of one of the knob masks; and (c) a pair of toggles, each toggle being configured to engage with one member of a pair of pawl members while disengaging with the other member of the pawl member pair; and (d) an attachment apparatus, comprising: at least one fastener configured to releasably secure the apparatus to the endoscope.

In one aspect, the self-locking mechanism assembly within the attachment apparatus kit for modifying the endoscope further comprises:

i. at least one housing unit;

ii. at least one fastener for the self-locking mechanism to be releasably secured to the endoscope;

iii. at least one rotatable pawl member is secured inside at least one housing unit which can be actuated by an actuator to communicate with the teeth-like protrusions on knob masks to engage the self-locking mechanism;

iv. an actuator, which pushes against a backside of the at least one pawl member to position the tip of the at least one pawl member toward the self-locking mechanism, which can be resisted by one or more leaflets of one or more toggles; and v. one or more toggles, secured inside at least one housing unit between at least one pair of pawl members with one or more leaflets of the toggle protruding outward to engage with the at least one pawl member.

Numerous modifications and variations of the present invention are possible in light of the above teachings. It is therefore to be understood that within the scope of the appended claims, the invention may be practiced otherwise than as specifically described herein.

What is claimed is:

1. An endoscope modified with an ergonomic attachment apparatus kit for mechanically assisting operation of the endoscope angulation control knobs, said kit, comprising:

(a) a pair of knob masks mounted onto or around the endoscope angulation control knobs, each mask, further comprising:

i. at least one tooth-like protrusion around the circumference of the knob mask for communication with a self-locking mechanism assembly, and ii. at least one finger grip interface for turning the knob mask;

(b) a self-locking mechanism assembly, comprising: at least one detent member that is configured to engage with the at least one tooth-like protrusion of each knob mask to lock the endoscope angulation control knob position in place;

(c) one or more toggles that provide engagement with the at least one detent member, by engaging or disengaging communication between the at least one detent member and the at least one tooth-like protrusion of each knob mask, allowing control over the bidirectional rotation and locking of the corresponding endoscope angulation control knob; and (d) an attachment apparatus, comprising: at least one fastener configured to releasably secure the apparatus to the endoscope.

2. The modified endoscope of claim 1, wherein, the pair of knob masks, comprises:
  i. a first mask, configured to mate with the up/down angulation control knob of the endoscope and to rotate in unison with the up/down angulation control knob when turned; and,
  ii. a second mask, configured to mate with the left/right angulation control knob of the endoscope and rotate in unison with the left/right angulation control knob when turned.

3. The modified endoscope of claim 2, wherein the first and second masks each further comprise: an attachment interface configured to releasably secure onto the corresponding endoscope control knobs.

4. The modified endoscope of claim 2, wherein the first and second masks each further comprise: at least one anchor port configured to releasably mount the knob mask onto the corresponding endoscope angulation control knob, the at least one anchor port being located inwardly along the circumference of the knob mask.

5. The modified endoscope of claim 2, wherein the first and second masks each further comprise: at least one spring-loaded clamp to mount each knob mask onto the corresponding endoscope angulation control knob.

6. The modified endoscope of claim 2, wherein the first and second masks are sufficiently expandable to fit snugly around the angulation control knobs of the endoscope.

7. The modified endoscope of claim 2, wherein the first and second masks each further comprise: at least two parts configured to assemble around the corresponding angulation control knob.

8. The modified endoscope of claim 1, wherein the at least one tooth-like protrusion along the circumference of each knob mask is configured to communicate with and provide resistance to the at least one detent member to lock the corresponding endoscope angulation control knob in place.

9. The modified endoscope of claim 1, wherein each knob mask extends the diameter of which the operator can interact about a central axis of rotation around an endoscope angulation control knob, thereby providing a longer lever arm.

10. The modified endoscope of claim 1, wherein each knob mask is configured to reduce the amount of muscle exertion required to torque and rotate the corresponding endoscope control knob.

11. The modified endoscope of claim 1, wherein the finger grip interface is located around the circumference of each knob mask, and comprises:
  i. at least one teardrop-shaped indent or protrusion;
  ii. at least one scallop-shaped indent or protrusion;
  iii. at least one thumb-sized ridge indent or protrusion;
  iv. at least one flower petal-shaped indent or protrusion;
  v. at least one tooth-like protrusion or protrusion;
  vi. a smooth surface; or
  vii. a combination thereof.

12. The modified endoscope of claim 1, wherein the self-locking mechanism assembly, comprises:
  i. at least one housing unit;
  ii. the at least one detent member, which is secured inside the at least one housing unit that can be actuated by an actuator toggle to communicate with the at least one tooth-like protrusion on each knob mask to engage the self-locking mechanism;
  iii. at least one actuator toggle, which is secured inside the at least one housing unit to engage or disengage the communication between the at least one detent member and the at least one tooth-like protrusion on each of the pair of knob masks; and
  iv. at least one fastener configured to releasably secure the mechanism assembly to the endoscope.

13. The modified endoscope of claim 1, wherein the self-locking mechanism is operable by the same hand that turns the endoscope angulation control knobs.

14. The modified endoscope of claim 1, wherein, the at least one detent member, comprises:
  i. a first detent piston, configured to communicate, when actuated, with the at least one tooth-like protrusion of the first mask;
  ii. a second detent piston, configured to communicate, when actuated, with the at least one tooth-like protrusion of the second mask;
  iii. at least one compression spring, configured to surround the first and second detent pistons and push forward or retract the first and second detent pistons when the actuator toggle is toggled;
  iv. a semi-rigid plastic flipper that communicates with the at least one tooth-like protrusion of each knob mask to lock the position of the knob mask by undergoing elastic deformation;
  v. a stepper motor that locks the knob masks at precise steps by activating and deactivating a system of electromagnets;
  vi. a system of ratchets and pawls that interact with the at least one tooth-like protrusion of each knob mask to allow rotation in one direction while arresting the rotation in the other direction; or
  vii. a combination thereof.

15. The modified endoscope of claim 1, wherein the attachment apparatus, comprises:
  i. at least one attachment interface that snugly wraps around the left/right angulation control knob lock of the endoscope;
  ii. at least one attachment interface that snugly wraps around at least one switch or at least one valve of the endoscope;
  iii. at least one attachment interface that snugly wraps around at least one handle of the endoscope;
  iv. at least one attachment interface that snugly wraps around electrical cable of the endoscope;
  v. at least one attachment interface that locks onto the endoscope using magnetic means;
  vi. at least one attachment interface that clamps to the endoscope;
  vii. at least one attachment interface that straps to the endoscope;
  viii. at least one attachment interface that snaps onto the endoscope; or
  ix. a combination thereof.

16. An ergonomic attachment apparatus kit for modifying an endoscope, comprising:
  (a) a pair of knob masks, comprising:
    i. a first mask configured to mate with the up/down angulation control knob of the endoscope and to rotate in unison with the up/down angulation control knob when turned, the first mask, further comprising:
      A at least one tooth-like protrusion around the circumference of the knob mask for communication with a self-locking mechanism assembly, and
      B at least one finger grip interface for turning the knob mask;
    ii. a second mask configured to mate with the left/right angulation control knob of the endoscope and rotate in unison with the left/right angulation control knob when turned, the second mask, further comprising:

A at least one tooth-like protrusion around the circumference of the knob mask for communication with a self-locking mechanism assembly, and B at least one finger grip interface for turning the knob mask;

(b) a self-locking mechanism assembly, comprising: at least one detent member that is configured to engage with the at least one tooth-like protrusion of each knob mask to lock the corresponding endoscope angulation control knob position in place;

(c) one or more toggles that provide engagement with the at least one detent member, by engaging or disengaging communication between the at least one detent member and the at least one tooth-like protrusion of each knob mask, allowing control over the bidirectional rotation and locking of the endoscope angulation control knob; and (d) an attachment apparatus, comprising: at least one fastener configured to releasably secure the apparatus to the endoscope.

17. The kit of claim 16, wherein the finger grip interface is located around the circumference of each knob mask, and comprises:
   i. at least one teardrop-shaped indent or protrusion;
   ii. at least one scallop-shaped indent or protrusion;
   iii. at least one thumb-sized ridge indent or protrusion;
   iv. at least one flower petal-shaped indent or protrusion;
   v. at least one tooth-like protrusion or protrusion;
   vi. a smooth surface; or
   vii. a combination thereof.

18. The kit of claim 16, wherein the first and second masks, further comprise: an attachment interface configured to releasably secure onto the endoscope control knobs.

19. The kit of claim 16, wherein the self-locking assembly comprises:
   i. at least one housing unit;
   ii. the at least one detent member, which is secured inside the at least one housing unit that can be actuated by an actuator toggle to communicate with the at least one tooth-like protrusion on each knob mask to engage the self-locking mechanism;
   iii. at least one actuator toggle, which is secured inside the at least one housing unit to engage or disengage the communication between the at least one detent member and the at least one tooth-like protrusion on each of the pair of knob masks; and
   iv. at least one fastener configured to releasably secure the mechanism assembly to the endoscope.

20. The kit of claim 16, wherein the at least one detent member, comprises:
   i. a first detent piston, configured to communicate, when actuated, with the at least one tooth-like protrusion of the first mask;
   ii. a second detent piston, configured to communicate, when actuated, with the at least one tooth-like protrusion of the second mask;
   iii. at least one compression spring, configured to surround the first and second detent pistons and push forward or retract the first and second detent pistons when the actuator toggle is toggled;
   iv. a semi-rigid plastic flipper that communicates with the at least one tooth-like protrusion of each knob mask to lock the position of the knob mask by undergoing elastic deformation;
   v. a stepper motor that locks the knob masks at precise steps by activating and deactivating a system of electromagnets;
   vi. a system of ratchets and pawls that interact with the at least one tooth-like protrusion of each knob mask to allow rotation in one direction while arresting the rotation in the other direction; or
   vii. a combination thereof.

21. The kit of claim 16, wherein the at least one fastener, comprises:
   i. at least one attachment interface that snugly wraps around the left/right angulation control knob lock of the endoscope;
   ii. at least one attachment interface that snugly wraps around at least one switch or at least one valve of the endo scope;
   iii. at least one attachment interface that snugly wraps around at least one handle of the endoscope;
   iv. at least one attachment interface that snugly wraps around electrical cable of the endoscope;
   v. at least one attachment interface that locks onto the endo scope using magnetic means;
   vi. at least one attachment interface that clamps to the endoscope;
   vii. at least one attachment interface that straps to the endoscope;
   viii. at least one attachment interface that snaps onto the endoscope; or
   ix. a combination thereof.

* * * * *